(12) United States Patent
Miller et al.

(10) Patent No.: US 7,137,975 B2
(45) Date of Patent: Nov. 21, 2006

(54) METHOD FOR INCREASING THE BATTERY LIFE OF AN ALTERNATING CURRENT IONTOPHORESIS DEVICE USING A BARRIER-MODIFYING AGENT

(75) Inventors: David J. Miller, Bountiful, UT (US); William I. Higuchi, Salt Lake City, UT (US); Kevin Li, Salt Lake City, UT (US); Gordon L. Flynn, Ann Arbor, MI (US)

(73) Assignee: Aciont, Inc., Salt Lake City, UT (US)

( * ) Notice: Subject to any disclaimer, the term of this patent is extended or adjusted under 35 U.S.C. 154(b) by 701 days.

(21) Appl. No.: 10/014,741

(22) Filed: Dec. 10, 2001

(65) Prior Publication Data

US 2002/0161323 A1 Oct. 31, 2002

Related U.S. Application Data

(63) Continuation-in-part of application No. 09/783,138, filed on Feb. 13, 2001, now Pat. No. 6,512,950, and a continuation-in-part of application No. 09/783,696, filed on Feb. 13, 2001, now Pat. No. 6,496,728.

(51) Int. Cl.
  *A61M 31/00* (2006.01)
  *A61N 1/30* (2006.01)
(52) U.S. Cl. .......................... 604/501; 604/20
(58) Field of Classification Search .............. 604/20, 604/501; 607/115–116, 120; 435/173.5–173.7; 424/450, 455; 204/450
  See application file for complete search history.

(56) References Cited

U.S. PATENT DOCUMENTS

| | | | |
|---|---|---|---|
| 3,991,755 A | 11/1976 | Vernon et al. | |
| 4,141,359 A | 2/1979 | Jacobsen et al. | |
| 4,325,367 A | 4/1982 | Tapper | |
| 4,340,047 A | 7/1982 | Tapper et al. | |
| 4,406,658 A | 9/1983 | Lattin et al. | |
| 4,689,039 A | 8/1987 | Masaki | |
| 4,702,732 A | 10/1987 | Powers et al. | |
| 4,734,090 A | 3/1988 | Sibalis | |
| 4,752,285 A | 6/1988 | Petelenz et al. | |

(Continued)

FOREIGN PATENT DOCUMENTS

DE 4137960 A1 5/1993

(Continued)

OTHER PUBLICATIONS

Dalziel, et al. (1950), "Effect of Frequency On Perception Currents," *AIEE Transactions* 69:1162-1168.

(Continued)

*Primary Examiner*—Catherine S. Williams
(74) *Attorney, Agent, or Firm*—Thorpe North & Western LLP

(57) ABSTRACT

An iontophoretic method for transporting compounds of interest across a body tissue is provided. The method utilizes an AC signal in conjunction with a barrier-modifying agent such as a fatty acid, fatty alcohol, bile acid, surfactant, or the like. The method enables the maintenance of a substantially constant electrical state in a localized region of the tissue through which transport occurs, thereby allowing a compound of interest to be transported across the tissue in a controlled and predictable manner. The barrier-modifying agent reduces the time as well as the voltage level required to achieve a target electrical resistance, thereby reducing patient discomfort and increasing the battery life of the iontophoresis device.

27 Claims, 14 Drawing Sheets

U.S. PATENT DOCUMENTS

| | | |
|---|---|---|
| 4,764,164 A | 8/1988 | Sasaki |
| 4,786,278 A | 11/1988 | Masaki |
| 4,792,702 A | 12/1988 | Masaki |
| 4,850,956 A | 7/1989 | Bontemps |
| 4,931,046 A | 6/1990 | Newman |
| 5,002,527 A | 3/1991 | Reller et al. |
| 5,006,108 A | 4/1991 | LaPrade |
| 5,013,293 A | 5/1991 | Sibalis |
| 5,019,034 A | 5/1991 | Weaver et al. |
| 5,023,085 A | 6/1991 | Francoeur et al. |
| 5,036,861 A | 8/1991 | Sembrowich et al. |
| 5,042,975 A | 8/1991 | Chien et al. |
| 5,047,007 A | 9/1991 | McNichols et al. |
| 5,056,521 A | 10/1991 | Parsons et al. |
| 5,057,072 A | 10/1991 | Phipps |
| 5,140,985 A | 8/1992 | Schroeder et al. |
| 5,213,568 A | 5/1993 | Lattin et al. |
| 5,224,927 A * | 7/1993 | Tapper ................. 604/20 |
| 5,279,543 A | 1/1994 | Glikfeld et al. |
| 5,312,325 A | 5/1994 | Sibalis |
| 5,314,502 A | 5/1994 | McNichols et al. |
| 5,318,514 A | 6/1994 | Hofmann |
| 5,328,452 A | 7/1994 | Sibalis |
| 5,328,453 A | 7/1994 | Sibalis |
| 5,328,454 A | 7/1994 | Sibalis |
| 5,336,168 A | 8/1994 | Sibalis |
| 5,362,307 A | 11/1994 | Guy et al. |
| 5,372,579 A | 12/1994 | Sibalis |
| 5,391,195 A | 2/1995 | Van Groningen |
| 5,395,310 A | 3/1995 | Untereker et al. |
| 5,405,317 A | 4/1995 | Myers et al. |
| 5,415,629 A | 5/1995 | Henley |
| 5,421,817 A | 6/1995 | Liss et al. |
| 5,423,739 A | 6/1995 | Phipps et al. |
| 5,443,441 A | 8/1995 | De Claviere |
| 5,465,713 A | 11/1995 | Schoendorfer |
| 5,499,967 A | 3/1996 | Teillaud et al. |
| 5,538,503 A | 7/1996 | Henley |
| 5,571,149 A | 11/1996 | Liss et al. |
| 5,617,851 A | 4/1997 | Lipkovker |
| 5,620,580 A | 4/1997 | Okabe et al. |
| 5,645,526 A | 7/1997 | Flower |
| 5,658,247 A | 8/1997 | Henley |
| 5,667,487 A | 9/1997 | Henley |
| 5,668,170 A * | 9/1997 | Gyory ................. 514/449 |
| 5,676,144 A | 10/1997 | Schoendorfer |
| 5,722,397 A | 3/1998 | Eppstein |
| 5,730,714 A | 3/1998 | Guy et al. |
| 5,771,890 A | 6/1998 | Tamada |
| 5,817,012 A | 10/1998 | Schoendorfer |
| 5,827,181 A | 10/1998 | Dias et al. |
| 5,885,211 A | 3/1999 | Eppstein et al. |
| 5,899,876 A | 5/1999 | Flower |
| 5,911,223 A * | 6/1999 | Weaver et al. ............ 128/898 |
| 5,928,571 A | 7/1999 | Chan |
| 5,944,662 A | 8/1999 | Schoendorfer |
| 5,947,921 A | 9/1999 | Johnson et al. |
| 5,954,685 A | 9/1999 | Tierney |
| 5,968,006 A | 10/1999 | Hofmann |
| 5,978,701 A | 11/1999 | Johnson et al. |
| 5,983,131 A | 11/1999 | Weaver et al. |
| 5,985,316 A * | 11/1999 | Gyory et al. ............ 424/449 |
| 5,989,409 A | 11/1999 | Kurnik et al. |
| 5,990,179 A * | 11/1999 | Gyory et al. ............ 514/329 |
| 5,991,655 A | 11/1999 | Gross et al. |
| 5,997,501 A | 12/1999 | Gross et al. |
| 6,006,130 A | 12/1999 | Higo et al. |
| 6,010,613 A | 1/2000 | Walters et al. |
| 6,018,679 A | 1/2000 | Dinh et al. |
| 6,023,629 A | 2/2000 | Tamada |
| 6,041,252 A | 3/2000 | Walker et al. |
| 6,041,253 A | 3/2000 | Kost et al. |
| 6,048,337 A | 4/2000 | Svedman |
| 6,083,190 A * | 7/2000 | Gyory et al. ............ 604/20 |
| 6,553,253 B1 * | 4/2003 | Chang ............ 604/20 |

FOREIGN PATENT DOCUMENTS

| | | |
|---|---|---|
| EP | 0254166 A2 | 1/1988 |
| EP | 0266083 A1 | 5/1988 |
| EP | 0308572 A2 | 3/1989 |
| EP | 0468636 A1 | 1/1992 |
| EP | 0847775 A1 | 6/1998 |
| GB | 2177928 A | 2/1987 |
| JP | 409276416 A | 10/1977 |
| JP | 402124176 A | 5/1990 |
| JP | 402243168 A | 9/1990 |
| JP | 403045272 A | 2/1991 |
| JP | WO 92/18197 | 10/1992 |
| JP | 405049702 A | 3/1993 |
| JP | 407067971 A | 3/1995 |
| JP | 408052224 A | 2/1996 |
| JP | 408322948 A | 12/1996 |
| JP | 411019226 A | 1/1999 |
| WO | WO 88/00846 | 2/1988 |
| WO | WO 91/15256 | 10/1991 |
| WO | WO 91/15257 | 10/1991 |
| WO | WO 94/05368 | 3/1994 |
| WO | WO 94/28967 | 12/1994 |
| WO | WO 97/07853 | 3/1997 |
| WO | WO 98/14235 | 4/1998 |
| WO | WO 99/30773 | 6/1999 |
| WO | WO 99/43383 | 9/1999 |
| WO | WO 99/52589 | 10/1999 |

OTHER PUBLICATIONS

Dalziel, et al. (1956), "Let-Go Currents and Voltages," *AIEE Transactions* 75:49.56.

Delgado-Charro et al. (1994), "Characterization of Convective Solvent Flower During Iontophoresis," *Pharmaceutical Research* 11(7):929-935.

Higuchi et al. (1999), "Mechanistic Aspects of Iontophoresis In Human Epidermal Membrane," *Journal of Controlled Release* 62:13-23.

Kim et al. (1999), "Convective Solvent Flow Across the Skin During Iontophoresis," *Pharmaceutical Research* 10(9):1315-1319.

Li, et al. (1999), "Pore Induction in Human Epidermal Membrane During Low to Moderate Voltage Iontophoresis: A Study Using AC Iontophoresis," *Journal of Pharmaceutical Sciences* 88(4):419-427.

Li, et al. (1998), "Characterization of the Transport Pathways Induced During Lower Moderate Voltage Iontophoresis in Human Epidermal Membrane," *Journal of Pharmaceutical Sciences* 87(1):40-48.

Li, et al. (1998, "Lag Time Data for Characterizing the Pore Pathway of Intact and Chemically Pretreated Human Epidermal Membrane," *International Journal of Pharmaceutics* 170:93-108.

Li, et al. (1999), "Pore Charge Distribution Considerations in Human Epidermal Membrane Electroosmosis," *Journal of Pharmaceutical Sciences* 88(10):1044-1049.

Peck, et al. (1998), "Flux Enhancement Effects of Ionic Surfactants Upon Passive and Electroosmotic Transdermal Transport," *Journal of Pharmaceutical Sciences* 87(9):1161-1169.

Sharma, et al. (2000), "Transdermal Drug Delivery Using Electroporation. II. Factors Influencing Skin Reversibility In Electroporative Delivery of Terazosin Hydrochloride in Hairless Rats," *Journal of Pharmaceutical Sciences* 89(4):536-544.

van der Geest et al. (1996), "Iontophoresis of Bases, Nucleosides, and Nucleotides," *Pharmaceutical Research* 13(4):553-558.

* cited by examiner

METHOD FOR INCREASING THE BATTERY LIFE OF AN ALTERNATING CURRENT IONTOPHORESIS DEVICE USING A BARRIER-MODIFYING AGENT

CROSS-REFERENCE TO RELATED APPLICATIONS

This application is a Continuation-In-Part of U.S. application Ser. No. 09/783,138, entitled "Methods for Delivering Agents Using Alternating Current," filed Feb. 13, 2001, and U.S. application Ser. No. 09/783,696, entitled "Methods for Extracting Substances Using Alternating Current," filed Feb. 13, 2001, both of which are incorporated by reference herein in their entireties.

ACKNOWLEDGEMENT OF GOVERNMENT SUPPORT

This invention was made in part with U.S. Government support under Grant Number GM 43181 awarded by the National Institutes of Health. The Government has certain rights in this invention.

TECHNICAL FIELD

This invention relates generally to the use of iontophoresis for permeant transport and, more specifically, to a novel method for increasing battery life and increasing patient comfort during iontophoresis. This invention finds utility in any field wherein a compound of interest is administered to the body or extracted from the body via iontophoresis, such as in the fields of drug administration, glucose monitoring, and therapeutic drug monitoring.

BACKGROUND

The transport of various compounds such as endogenous species, metabolites, drugs and nutrients across body such as the skin or mucosal tissue is primarily a function of three factors: tissue permeability, the presence, absence, and magnitude of a driving force, and the size of the area through which transport occurs. Body tissues such as skin and mucosal tissue are generally not sufficiently permeable to allow passive transport of molecules therethrough. That is, the permeability of many tissues is low because membranes are composed of cells and intercellular matrices that are relatively impermeable to ionized and uncharged polar species. Thus, it is the cells of the stratum corneum that present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing that creates, in most cases, a substantially impermeable barrier to drug penetration. With many drugs, the rate of permeation through the skin is extremely low without the use of some means to enhance the permeability of the skin.

Iontophoresis is one approach that can be utilized to transport compounds of interest across a body tissue by the application of an electrical current. In practice, iontophoretic methods may involve positioning an electrode containing some type of drug reservoir or, in another modality of use, a collection chamber (e.g., an absorbent pad) on a body tissue, typically the skin or mucosa. A second distal electrode is placed in contact with the body tissue to complete the electrical circuit. The second electrode may also have delivery or sensing capabilities built in.

The problem with most iontophoretic devices, including constant current and constant conductance systems, is the substantial amount of energy required to achieve and maintain a target state of electroporation and transport rate. Iontophoresis can cause irritation, sensitization and pain in some patients, and the degree of irritation, sensitization and/or pain is, as a general rule, directly proportional to the applied current or voltage. For example, Dalziel and Massoglia showed a correlation between current intensity and the percentage of test subjects reporting perception of the current for both direct current (DC) and alternating current (AC). (Dalziel and Massoglia (1956) *AIEE Trans.* 75:49–56). Algom, Raphaeli, and Cohen-Raz found that pain perception increased as an exponential power function of the electrical current intensity. (Algom D, Raphaeli N, and Cohen-Raz L. Percept Mot Skills, Volume 65, Year 1987, Pages 619–25). Anigbogu et al. (Anigbogu et al. (2000) Int. J. Pharm. 200:195–206) showed that irritation in rabbit skin, as measured by erythema, transepidermal water loss and laser Doppler velocimetry, was directly related to the intensity of the applied electrical current.

The effects of the electrical current on sensitization have been investigated, resulting in attempts to develop iontophoretic devices and methods that are capable of maintaining the electrical current and/or potential at a comfortable level. For example, U.S. Pat. No. 5,246,418 to Haynes et al. discloses a method of reducing irritation during iontophoresis using a feedback circuit, which, during iontophoretic transport, enables control over the applied current and voltage.

A majority of the known iontophoretic methods utilize constant-current DC signals to effectuate transport. There are several problems associated with such methods that have resulted in limited acceptance by clinicians, patients and government regulators. One shortcoming of constant-current DC is that the rate of drug delivery changes with the passage of time, even though a constant current is applied. The inability to provide a constant flux at constant current is possibly due to time-dependent changes in tissue porosity, accompanying changes in pore surface charge density and effective pore size over the course of treatment. Such changes pose significant problems in effectively controlling the transdermal delivery of drugs by iontophoresis. It is generally observed that with constant-current DC methods the transference number (fraction of total current carried by a particular charged species) for the transported compound increases with time over the course of a typical iontophoresis procedure. This variability in transference number means that the amount of a compound of interest that is transported across a tissue varies with time and cannot be controlled or predicted effectively.

Problems in controlling the extent of electroporation with constant-current DC methods results in high inter-and intra-patient variability. Hence, not only does the amount of a compound transported vary as a function of time, there is further day-to-day variation for the same individual, as well as variation from person to person.

In an effort to overcome the limitations with constant current DC methods, methods that utilize AC current, either alone or in conjunction with a DC offset have been developed. Such methods are disclosed in copending U.S. application Ser. No. 09/783,138, entitled "Methods for Delivering Agents Using Alternating Current," filed Feb. 13, 2001, corresponding to International Patent Publication No. WO 01/60449, and in U.S. application Ser. No. 09/783,696, entitled "Methods for Extracting Substances Using Alternating Current," filed Feb. 13, 2001, corresponding to International Patent Publication No. WO 01/60448.

It has now been discovered that application of a barrier-modifying agent (also referred to herein as a "barrier-modifying agent" or "barrier modifier") to the body tissue, either prior to or during AC iontophoresis, lowers the potential voltage difference needed to achieve electroporation. As a result, the rate at which a compound of interest can be transported through the body tissue can be maintained using lower electrical voltage levels. This reduction in applied voltage ultimately results in increased battery life, extended treatment times, decreased treatment costs, and increases patient comfort.

SUMMARY OF THE INVENTION

An iontophoretic method is provided for transporting a compound of interest across a body tissue utilizing an AC signal in conjunction with a barrier-modifying agent. The method can be used to deliver or extract a number of different compounds, such as endogenous substances located within the body, pharmacologically active agents, markers of disease, and the like. During iontophoretic transport, the barrier-modifying agent reduces the voltage required to achieve a target flux rate while an AC signal is used to maintain a substantially constant electrical state in the localized region of tissue through which delivery or extraction occurs, thereby allowing compounds to be transported across the tissue in a controlled and predictable manner using less power. The method has utility in a wide range of applications, e.g., in therapeutic treatments, in detoxification methods, in pain management, in metabolite or therapeutic agent monitoring, and dermatological treatments. The method of the invention can also be utilized in diagnostic applications, e.g., to detect the presence of a disease marker.

More specifically, the invention involves iontophoretically transporting a compound of interest across a localized region of body tissue using an alternating current iontophoresis device in conjunction with a barrier-modifying agent. The barrier-modifying agent may be, for example, a fatty acid, fatty alcohol, surfactant, bile acid, bile salt, organic solvent or the like. The AC signal is adjusted so as to maintain a substantially constant electrical state within a localized region of a patient's body tissue, wherein maintenance of the substantially constant electrical state is carried out at a reduced voltage level while facilitating transport of a compound of interest across the tissue. The AC signal is typically adjusted to maintain a substantially constant state of electroporation in the localized region of tissue throughout the time period in which the compound is delivered. The electrical state that is maintained by the AC signal is electrical conductance or electrical resistance, generally the latter. The AC signal applied to the tissue can have essentially any waveform. The waveform can be symmetric or asymmetric, thus including square, sinusoidal, saw-tooth, triangular and trapezoidal shapes, for example. The frequency of the AC signal tends to be at least about 1 Hz, although in other instances the frequency is within the range of about 1 Hz to about 1 kHz, about 1 kHz to about 10 kHz, or about 10 kHz to about 30 kHz. Generally, the barrier-modifying agent decreases the time to reach a target resistance level, e.g., 5 k$\Omega$, by at least 20%, preferably by at least 50%, and most preferably by at least 70%.

Optionally, an electrical prepulse may be applied to the tissue after administration of the barrier-modifying agent and prior to the AC signal to induce electroporation within the region of the tissue through which delivery is to occur. The prepulse can be either an AC signal or a DC signal. In the absence of a barrier-modifying agent, the required voltage of the prepulse could be as high as 90 V. See WO 01/60448 and WO 01/60449, cited supra. With the barrier-modifying agent, however, the required voltage is reduced by at least 20%, preferably by at least 50%, and most preferably by at least 70%. Typically, this means that the required voltage will be in the range of about 1 V to about 75 V, in some instances in the range of about 1 V to about 45 V, preferably in the range of about 1 V to about 10 V. The lowered voltage requirement in turn minimizes the likelihood of patient discomfort. In addition, by reducing power requirements, the invention provides for an increase in the battery life of an iontophoretic device and decreases the cost of treatment.

Transport of a compound of interest across the tissue can be via diffusion through an electroporated region solely induced by the AC signal. Alternatively, a DC offset signal can be applied in combination with the AC signal. The DC offset signal is effective to promote transport of a compound through a localized region of body tissue. When combined with an AC signal, which maintains the region at a substantially constant electrical state, a relatively constant and reproducible rate of transport can be realized. The DC offset signal is typically applied substantially continuously during iontophoretic transport and is of a voltage or current effective to control the rate of delivery. The DC offset signal is usually in the range of about 0.1 to 10 V and about 0.01 to 0.5 mA/cm$^2$, but can include any particular voltage, current or range of voltages or currents. In certain methods, the DC offset signal is applied utilizing two electrodes in contact with the tissue and the direction of current flow of the DC offset signal is periodically reversed between the two electrodes. The method may also involve application of both an electrical prepulse and a DC offset with the AC signal. In this case, the electrical prepulse will generally, although not necessarily, be applied to the tissue after administration of the barrier-modifying agent and prior to application of the AC signal, so as to induce electroporation within the region.

The method of the invention can be utilized with a variety of different types of tissue, including both animal and plant tissues. The tissues can be part of a body surface or artificial. Usually the tissue is skin or mucosal tissue, particularly human skin or mucosal tissue. A variety of compounds can be transported across a body surface in the manner, including both charged and uncharged agents.

DETAILED DESCRIPTION OF THE INVENTION

I. Definitions and Nomenclature

Figure 1:
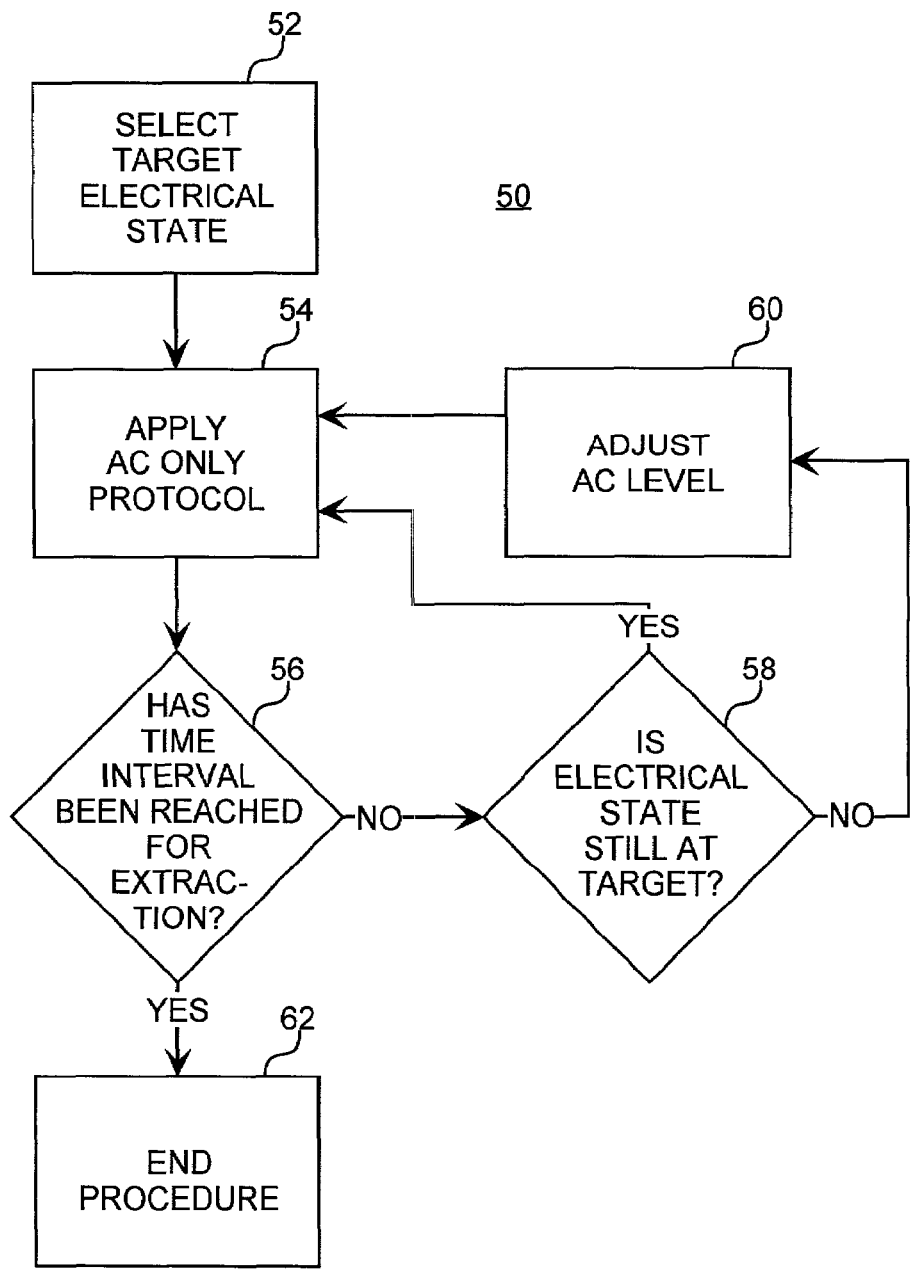
FIG. 1 is a schematic block diagram illustrating steps in a method utilizing only an AC signal to transport a compound of interest across a localized region of body tissue as provided herein.

Before describing the present invention in detail, it is to be understood that this invention is not limited to specific drug delivery systems, reverse iontophoresis extraction systems, iontophoresis device structures, barrier-modifying agents, carriers, or the like, as such may vary. It is also to be understood that the terminology used herein is for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a barrier-modifying agent" includes a mixture of two or more barrier-modifying agents as well as a single such agent, reference to "an analyte" includes one or more analytes, and the like.

In describing and claiming the present invention, the following terminology will be used in accordance with the definitions set out below.

Herein the terms "iontophoresis" and "iontophoretic" are used to refer to the transdermal delivery of pharmaceutically active agents by means of an applied electromotive force to an agent-containing reservoir. The terms "iontophoresis" and "iontophoretic" are also meant to refer to "reverse iontophoresis," "reverse iontophoretic," "electroosmosis," and "iontohydrokinesis" or "iontohydrokinetic." The terms "reverse iontophoresis," "reverse iontophoretic," and "analyte extraction" are used to refer to the collection of analytes from the body to an analyte-collecting reservoir by means of an applied electromotive force.

The terms "current" and "electrical current," when used to refer to the conductance of electricity by movement of charged particles, are not limited to "direct electrical current," "direct current," or "constant current." The terms "current" or "electrical current" should also be interpreted to include "alternating current," "alternating electrical current," "alternating current with direct current offset," "pulsed alternating current," and "pulsed direct current."

During iontophoresis, certain modifications or alterations of the skin occur, for example, changes in permeability, due to mechanisms such as the formation of transiently existing pores in the skin, also referred to as "electroporation." Any electrically assisted transport of species enhanced by modifications or alterations to the body surface (e.g., formation of pores in the skin and "electroporation") are also included in the term "electrotransport" as used herein. Thus, as used herein, the terms "electrotransport," "iontophoresis, " and "iontophoretic," further refer to the transport of permeants by the application of an electric field regardless of the mechanisms.

The term "pore" is used to describe any transport pathway through the tissue, whether endogenous to the tissue or formed by electroporation.

As used herein, a "body tissue" refers to an aggregation of similar cells and/or cell components united in performance of a particular function. The tissue can be part of a living organism, a section excised from a living organism, or artificial. Typically, however, the body tissue will be the body surface of a human patient, i.e., the skin, the mucosal tissue, the ocular surface, etc. Unless otherwise indicated, and "body surface" are used to refer to skin or mucosal tissue, including the interior surface of body cavities that have a mucosal lining. Unless otherwise indicated, the term "skin" should be interpreted as including "mucosal tissue" and vice versa.

A "localized region" of a tissue refers to the area or section of a body tissue that is electroporated via the application of one or more electrical signals and through which a compound of interest is transported. Thus, a localized region of a body surface refers to an area of skin or mucosal tissue through which an active agent is delivered or an analyte is extracted.

The term "transport," as in the "transport" of a compound of interest across a body tissue, refers to passage of the compound in either direction, i.e., the compound may be delivered to the patient from an external source, across the skin or mucosal tissue, or it may be extracted from beneath the patient's body surface, as in analyte extraction.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The term "treatment" is also used to refer to the extraction of a substance through a body tissue for the purpose of quantitative or qualitative analysis.

The terms "drug," "active agent," and "pharmacologically active agent" are used interchangeably herein to refer to any chemical compound, complex or composition that is suitable for topical, transdermal, or transmucosal administration and that has a beneficial biological effect, preferably a therapeutic effect in the treatment of a disease or abnormal physiological condition, although the effect may also be prophylactic in nature. The terms also encompass agents that are administered for nutritive or diagnostic purposes, e.g., nutrients, dietary supplements and imaging agents. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

The term "analyte" is used to refer to a compound of interest to be iontophoretically extracted from beneath a localized region of a patient's body surface. When particular types of analytes are mentioned, it is to be understood that salts, esters, amides, analogs, conjugates, metabolites and other derivatives are included unless otherwise indicated.

The term "barrier-modifying agent" refers to a compound or composition that is effective to alter the inherent barrier of a body tissue so as to facilitate transport of a compound of interest therethrough. That is, a body tissue such as the skin or mucosa has a barrier that limits the transport of an active agent into or through the body tissue. For example, with skin, the stratum corneum serves as a cutaneous barrier into which most applied compounds and compositions will not penetrate. A barrier-modifying agent, in this context, is a compound that alters the stratum corneum so as to facilitate the transdermal transport of an active agent to be delivered or an analyte to be extracted. Cutaneous barrier modifiers generally disrupt the stratum corneum barrier function by inserting into or otherwise disrupting the lipid bilayer structure in the intercellular regions within the stratum corneum, by inducing hydration and/or swelling of the lipid bilayer, by denaturing epidermal keratin, and/or by facilitating solubilization of the compound to be transported.

The terms "optional" and "optionally" mean that the subsequently described circumstance may or may not occur, so that the description includes instances where the circumstance occurs and instances where it does not. For example, recitation of an "optional" DC offset encompasses an iontophoretic process without a DC offset as well as an iontophoretic process with a DC offset.

It must be noted that the invention is not limited to constant current or direct current iontophoretic methods, but encompasses alternating current iontophoresis as well as AC iontophoresis with a direct current offset.

II. Overview of AC Iontophoresis

As discussed in International Patent Publications WO 01/60448 and WO 01/60449, supra, an AC signal alone or in combination with one or more other signals, AC or DC, can be utilized to induce and maintain a substantially constant electrical state in a localized region of a tissue through which transport occurs. By maintaining such an electrical state, one can maintain the permeability of the tissue within the region such that pore size, pore density and surface charge density of pores within the region are kept constant. The process of applying an electrical signal to create new pores or enlarge existing pores within a tissue is referred to as electroporation, and the degree of permeability so obtained is referred to as the state of electroporation.

Controlling tissue permeability or electroporative state in this manner enables one to reduce variability in the flux of an agent across the tissue such that a constant transference number is achieved for the agent being transported. Reduction in flux variability in turn means that one can deliver agents such as pharmaceuticals in a controlled and predictable way, an aspect that is particularly important for pharmaceuticals having a narrow therapeutic window. Intra- and inter-patient variability in the rate of drug delivery can also be minimized using certain methods disclosed herein.

Application of a barrier-modifying agent, either prior to, during, or both prior to and during application of the AC signal, has now been found to be effective in decreasing the amount of current required to achieve and sustain electroporation. Decreasing the required current requirement not only reduces patient discomfort, but also extends battery life in iontophoretic devices.

The power of the electrical output is defined as a product of the voltage and current:

$$W = V \times I \qquad (1)$$

where W is the power, V is the voltage, and I is the current. From Ohm's law, the current is defined as:

$$I = \frac{V}{R} \qquad (2)$$

where R is the resistance. Substituting equation (1) into equation (2) provides (3)

$$W = \frac{V^2}{R} \qquad (3)$$

It has been found that by using barrier-modifying agents in conjunction with AC iontophoresis, the power requirement can be decreased consistent with the above modeling. Although the aforementioned theory is generally applicable to iontophoretic systems, it will specifically provide benefits for iontophoresis systems employing AC current.

While the AC signal is adjusted to maintain a substantially constant electrical state, transport of a compound of interest across the tissue can be accomplished in various ways. If the concentration of the compound on one side of a tissue is significantly higher than on the other side of the tissue (e.g., the skin surface, or exterior, relative to the interior or underside), transport of an agent through the electroporated region can be achieved by passive Fickian-driven diffusion. Other methods increase the rate of transport by applying a DC offset of the AC signal to the electroporated region to drive the agent through the region. The electrical state and thus the degree of electroporation of a tissue can be ascertained by monitoring the electrical conductance or resistance of the tissue or by monitoring other electrical parameters that correlate with the degree of cell permeability.

An optional prepulse can be applied to the body tissue in order to quickly attain a desired electrical state that is then maintained with the AC signal. The prepulse can be either an AC or DC signal. Hence, the methods provided herein can include simply an AC signal ("AC protocol" or "AC-only protocol"), or a combination of an AC signal and a DC offset signal ("AC plus DC offset protocol"), either of which can be further combined with an AC or DC prepulse. The presence of the barrier-modifying agent enables a lower level of current to achieve the desired electrical state, for both the AC signal and the optional prepulse, as the barrier-modifying agent reduces the electrical potential needed to lower the resistance of the tissue to a target resistance. The methods described in WO 01/60448 and WO 01/60449 and used herein differ significantly from conventional DC or pulsed DC iontophoretic delivery and extraction methods. As described supra, a significant shortcoming with constant current DC methods and pulsed DC methods is their failure to maintain a constant state of tissue permeability or electroporation. Often the pores within the region of the electroporated tissue change with time during iontophoresis, resulting in a concomitant change in the permeability of the electroporated region. The inability to maintain a substantially constant electroporated state severely limits the ability of constant current DC methods to controllably and predictably deliver an agent across a tissue. The methodology used in conjunction with the present invention, which provides for a substantially constant electrical state during the period in which transfer occurs, can ameliorate this problem.

III. The Barrier-modifying Agent

Modifiers of the penetration barrier act to increase the permeability of the tissue to the agent being transported therethrough. These barrier modifiers will generally, although not necessarily, be modifiers of the cutaneous barrier, wherein permeability of the outer layer of the skin can be enhanced in at least one of several ways. That is, the barrier modifiers may act as lipid bilayer disrupting agents by inserting into or otherwise disrupting the bilayer structure in the intercellular spaces of the stratum corneum. Other barrier modifiers may cause hydration and/or swelling of the lipid bilayer, facilitating passage of certain types of compounds. Still other barrier modifiers may alter the helical keratinous filaments of the stratum corneum, as thought to be the case with certain anionic surfactants. Finally, any or all of these barrier modifiers may also facilitate solubilization of the transported molecule, which in turn promotes transport through the body tissues. The barrier-modifying agent may be delivered to the body tissue prior to, during, or both prior to and during application of the AC electrical signal. If administered prior to iontophoresis, the barrier-modifying agent may be applied alone or in a suitable carrier system. If the barrier modifier is to be administered concurrently with iontophoresis, the agent may be contained within the iontophoretic device, as discussed infra.

In general, the barrier-modifying agent is selected from one of the following groups: fatty acids; fatty alcohols; bile acids and bile salts; nonionic surfactants; anionic surfactants; cationic and amphoteric surfactants; hydrocarbon solvents; esters and amides; pyrrolidones; sulfoxides; cyclodextrins; alkyl N,N-disubstituted amino esters; N-alkyl-azacycloalkanones and N-alkyl-azacycloalkenones; terpenes; and urea and its derivatives.

(1) Fatty acids: Fatty acids useful as barrier modifiers herein include both saturated or unsaturated fatty acids. Examples of suitable fatty acids include, but are not limited to, arachidic acid (n-eicosanoic acid), arachidonic acid, behenic acid (docosanoic acid), capric acid (n-decanoic acid), caproic acid (n-hexanoic acid), caproleic acid (9-decenoic acid), caprilic acid (n-octanoic acid), docosadienoic acid, docosahexaenoic acid, docosapentaenoic acid, eicosadienoic acid, eicosahexaenoic acid, eicosapentaenoic acid, eicosatrienoic acid, elaidic acid (trans-9-octadecanoic acid), eleosteroic acid, erucic acid (13-docosenoic acid), heneicosanoic acid, heptacosanoic acid, heptadecanoic acid, heptanoic acid, hexacosanoic acid, isostearic acid, lauric acid (n-dodecanoic acid), lignoceric acid (n-tetracosanoic acid), linoleic acid, linolelaidic acid, α-linolenic acid, γ-linolenic acid, myristic acid (n-tetradecanoic acid), myristoleic acid, neodecanoic acid, nervonic acid (cis-15-tetracosenoic acid), nonacosanoic acid, nonadecanoic acid, octacosanoic acid, oleic acid, palmitic acid (n-hexadecanoic acid), palmitoleic acid, pelargonic acid (nonanoic acid), pentadecanoic acid, pentacosanoic acid, petroselenic acid, phytanic acid, stearic acid (n-octadecanoic acid), triacontanoic acid, tricosanoic acid, tridecanoic acid, and undecanoic acid, vaccenic acid. $C_{10}$–$C_{18}$ fatty acids are preferred, and of these, capric acid, lauric acid, and oleic acid, are particularly preferred.

(2) Fatty alcohols: Fatty alcohols are also suitable barrier modifiers, and derive from the fatty acids above, i.e., the terminal carboxylic acid group COOH of the fatty acid is replaced with a $CH_2OH$ group. Examples include behenyl alcohol, cetyl alcohol, elaidyl alcohol, erucyl alcohol, isostearyl alcohol, lauryl alcohol, myristyl alcohol, oleyl alcohol, palmitoleyl alcohol, petroselinyl alcohol, and stearyl alcohol.

(3) Bile salts and bile acids: Bile acids are naturally occurring surfactants having a cholanic acid nucleus and are substituted with a 3α-hydroxyl group and optionally with other hydroxyl groups as well, typically at the $C_6$, $C_7$ or $C_{12}$ position of the sterol nucleus. Bile acids include, for example, cholic acid, deoxycholic acid, lithocholic acid, chenodeoxycholic acid (also referred to as "chenodiol" or "chenic acid"), and ursodeoxycholic acid. The aforementioned acids are "unconjugated" bile acids in that the carboxyl group extending from the $C_{17}$ position of the sterol nucleus is in free acid form. Bile acids may also be "conjugated," typically by reaction of the aforementioned carboxyl group with the free amine moiety of glycine ($H_2NCH_2COOH$) or taurine ($H_2NCH_2CH_2SO_3H$) to form a peptide linkage. Conjugated bile acids thus include, for example, taurocholic acid, taurodeoxycholic acid, taurolithocholic acid, taurochenodeoxycholic acid, tauroursodeoxycholic acid, glycocholic acid, glycodeoxycholic acid, glycolithocholic acid, glycochenodeoxycholic acid, and glycoursodeoxycholic acid. Any of the aforementioned bile acids can be advantageously used in conjunction with the present invention. The bile acids may also be in the form of a salt, in which case the acidic functionality is ionized and associated with a cationic counter-ion, e.g., sodium, potassium, ammonium, or the like. Examples of bile salts useful herein include, but are not limited to, sodium cholate, sodium taurocholate, sodium glycocholate, sodium deoxycholate, sodium taurodeoxycholate, sodium glycodeoxycholate, sodium ursodeoxycholate, sodium chenodexoycholate, sodium taurochenodeoxycholate, sodium taurochenodeoxycholate, and sodium N-methyl taurocholate.

(4) Nonionic surfactants: The barrier modifier may also be a nonionic surfactant. A number of compounds are typically classified as "nonionic" surfactants, including those identified below:

(A) Esters of fatty acids wherein the carboxylic acid groups —COOH of fatty acids are replaced with esters —COOR where R is a long-chain substituent or a lower alkyl group, examples being cetyl lactate, myristyl lactate, lauryl lactate, isostearyl lactate, and stearyl lactate, ethyl lactate, isopropyl myristate, isopropyl palmitate, ethyl linoleate, and isopropyl linoleate.

(B) Fatty (long-chain alkyl or alkenyl) esters of monohydric alcohols, diols, and polyols. Here, the hydroxyl groups —OH of alcohols are replaced with —O—(CO)—L—CH$_3$ ("fatty") groups where L is alkylene or alkenylene containing 1 to 3 double bonds and from about 6 to about 22 carbon atoms. Examples of monohydric alcohols include fatty alcohols, as discussed above, monohydric sterols such as cholesterol, and lower alcohols (i.e., alcohols containing less than ten carbon atoms) such as n-propanol, isopropanol, n-butanol, isobutanol, phenol, benzyl alcohol, phenyl ethanol, menthol, 1-dodecanol, and lactic acid. Examples of diols and polyols (generally $C_2$–$C_{24}$) include: glycerol; butane diol; alkylene glycols such as propylene glycol, ethylene glycol, diethylene glycol, polyethylene glycol, and polypropylene glycol; monomeric polyols such as trimethylol ethane, trimethylol propane, trimethylol butane, pentaerythritol and dipentaerythritol; and sugar alcohols containing 5 to 12 carbon atoms such as sorbitol or mannitol; sugars containing 5 to 12 carbon atoms such as glucose or sucrose. Specific examples of nonionic surfactants within this group are as follows: methyl laurate, ethyl oleate, isopropyl n-decanoate, isopropyl myristate, isopropyl palmitate, sucrose monooleate, cholesterol stearate, octyldoclecyl myristate, propylene glycol dilaurate, propylene glycol monooleate, propylene glycol dioctanoate, propylene glycol dicaprylate, propylene glycol dicaprate, glycerol monolaurate, glycerol monooleate, glycerol monostearate; the sorbitan fatty acid esters sorbitan monopalmitate, sorbitan monooleate, sorbitan dioleate, sorbitan trioleate, sorbitan sesquioleate, sorbitan isostearate, sorbitan diisostearate, sorbitan tristearate, and sorbitan monolaurate; and the sucrose fatty acid esters sucrose monooleate, sucrose monostearate, sucrose monolaurate, sucrose distearate, sucrose dipalmitate, and sucrose monopalmitate.

(C) Diols and polyols that are both esterified with a fatty acid and substituted with a polyoxyalkylene. These include, without limitation, polyoxyethylene and polyoxypropylene glyceryl stearate, laurate, and palmitate, e.g., polyethylene glycol (PEG)-20 glyceryl stearate, polypropylene glycol PPG-10 glyceryl stearate, PEG-15 glyceryl laurate, PEG-20 glyceryl laurate, PEG-30 glyceryl laurate, PEG-40 sorbitol septaoleate, PEG-40 glyceryl laurate; and polyoxyethylene sorbitan fatty acid esters (polysorbates) and polyoxypropylene sorbitan fatty acid esters. Polyoxyethylene sorbitan esters include sorbitan oleates, palmitates and stearates, e.g., polyoxyethylene sorbitan monolaurate (for example, PEG-20 sorbitan monolaurate, available commercially under the tradename Tween®-20), polyoxyethylene sorbitan monopalmitate (for example, PEG-20 sorbitan monopalmitate, available commercially under the tradename Tween®-40), polyoxyethylene sorbitan monostearate (for example, PEG-20 sorbitan monostearate, available commercially under the tradename Tween®-60), polyoxyethylene sorbitan monooleate (for example, PEG-20 sorbitan monooleate, available commercially under the tradename Tween®-80), polyoxyethylene sorbitan trioleate (e.g., PEG-20 sorbitan trioleate), polyoxyethylene sorbitol septaoleate, and polyoxyethylene sorbitan monooleate. Polyoxypropylene sorbitan fatty acid esters include, by way of example, polyoxypropylene sorbitan monooleate, polyoxypropylene sorbitan monopalmitate, polyoxypropylene sorbitan trioleate, and polyoxypropylene sorbitol septaoleate.

(D) Polyoxyalkylene fatty acid esters such as polyoxyethylene fatty acid esters and polyoxypropylene fatty acid esters, e.g., polyethylene glycol (PEG)-2 stearate, PEG-2 oleate, PEG-4 stearate, PEG-4 laurate, PEG-4-ricinoleate, PEG-4 dioleate, PEG-4 distearate, PEG-4 dilaurate, PEG-6 stearate, PEG-6 dioleate, PEG-6 distearate, PEG-6 dilaurate, PEG-8 stearate, PEG-8 laurate, PEG-8 oleate, PEG-8 dilaurate, PEG-8 dioleate, PEG-8 distearate, PEG-10 stearate, PEG-10 laurate, PEG-10 oleate, PEG-10 dipalmitate, PEG-10 distearate, PEG-12 stearate, PEG-12 oleate, PEG-12 ricinoleate, PEG-12 distearate, PEG-12 dilaurate, PEG-12 dioleate, PEG-20 stearate, PEG-20 oleate, PEG-20 dilaurate, PEG-20 dioleate, PEG-20 distearate, PEG-25 stearate, PEG-30 stearate, PEG-30 cholestanol, PEG-32 oleate, PEG-32 laurate, PEG-32 stearate, PEG-32 dilaurate, PEG-32 dioleate, PEG-32 distearate, PEG-40 laurate, PEG-40 oleate, PEG-40 stearate, PEG-400 dioleate, and PEG-400 distearate.

(E) Polyoxyalkylene fatty ethers. These are condensation products of alkylene oxides and fatty alcohols, such as diethyleneglycol lauryl ether (PEG-2-L), PEG-24 cholesterol ether, PEG-2 oleyl ether, PEG-3 oleyl ether, PEG-5 oleyl ether, PEG-10 oleyl ether, PEG-20 oleyl ether, PEG-4 lauryl ether, PEG-9 lauryl ether, PEG-23 lauryl ether, PEG-2 cetyl ether, PEG-10 cetyl ether, PEG-20 cetyl ether, PEG-2 stearyl ether, PEG-10 stearyl ether, PEG-20 stearyl ether, and PEG-100 stearyl ether.

(F) Polyglyceryl fatty acid esters such as polyglyceryl-2 stearate, polyglyceryl-2 oleate, polyglyceryl-2 isostearate, polyglyceryl-3 oleate, polyglyceryl-4 oleate, polyglyceryl-4 stearate, polyglyceryl-6 oleate, polyglyceryl-10 laurate, polyglyceryl-10 oleate, polyglyceryl-10 stearate, polyglyceryl-6 ricinoleate, polyglyceryl-10 linoleate, polyglyceryl-6 pentaoleate, polyglyceryl-3 dioleate, polyglyceryl-3 distearate, polyglyceryl-4 pentaoleate, polyglyceryl-6 dioleate, polyglyceryl-2 dioleate, polyglyceryl-10 trioleate, polyglyceryl-10 pentaoleate, polyglyceryl-10 septaoleate, polyglyceryl-10 tetraoleate, polyglyceryl-10 decaisostearate, and polyglyceryl-10 decaoleate.

(5) Anionic surfactants: Anionic surfactants that may serve as the barrier modifier include, without limitation, long-chain alkyl sulfonates, carboxylates and sulfates, as well as alkyl aryl sulfonates and the like. Preferred anionic surfactants include, by way of example, sodium n-dodecyl sulfate, dialkyl sodium sulfosuccinates (e.g., sodium bis-(2-ethylhexyl)-sulfosuccinate), sodium lauryl sulfate, sodium 7-ethyl-2-methyl-4-dodecyl sulfate, lithium n-dodecyl sulfate, sodium dodecylbenzene sulfonate, sodium oleate, sodium caprate, sodium laurate, sodium lauryl sarcosinate, sodium dioctyl sulfosuccinate, sodium caproate, sodium caprylate, sodium myristate, sodium myristolate, sodium palmitate, sodium palmitoleate, sodium ricinoleate, sodium linoleate, sodium linolenate, sodium stearate, sodium tetradecyl sulfate, sodium lauryl sarcosinate, and sodium dioctyl sulfosuccinate (sodium docusate).

(6) Cationic and amphoteric surfactants: Suitable cationic surfactants are generally long-chain amine salts or quaternary ammonium salts, wherein the quaternary ammonium salts are generally selected from mono $C_6$–$C_{16}$, preferably $C_6$–$C_{10}$, N-alkyl or alkenyl ammonium surfactants wherein remaining N positions are substituted by methyl, hydroxyethyl or hydroxypropyl groups. Examples of cationic surfactants include, without limitation, decyltrimethylammonium bromide, dodecyltrimethylammonium bromide, hexadecyltriammonium bromide, tetradecyltrimethylammonium bromide, tetradecyltrimethylammonium chloride, dodecylammonium chloride, alkyl benzyldimethylammonium chlorides, diisobutyl phenoxyethoxydimethyl benzylammonium salts, and alkylpyridinium salts. Amphoteric surfactants are generally, although not necessarily, compounds that include a carboxylate or phosphate group as the anion and a charged amino or quaternary ammonium moiety as the cation. Examples of betaines useful herein include cocodimethyl carboxymethyl betaine, cocoamidopropyl betaine, cocobetaine, lauryl amidopropyl betaine, oleyl betaine, lauryl dimethyl carboxymethyl betaine, lauryl dimethyl c-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and the sulfobetaines cocodimethylsulfopropyl betaine, stearyl dimethylsulfopropyl betaine, lauryl dimethylsulfoethyl betaine, and lauryl bis-(2-hydroxyethyl)sulfopropyl betaine. Other amphoteric surfactants include, for example, lauryldimethylamine oxide, n-dodecyl-N,N-dimethylamino glycine, and 3-dodecyl-dimethylammoniopropane-1-sulfonate.

(7) Hydrocarbon solvents: Hydrocarbon solvents can also serve as the barrier modifier herein, and include, by way of example, linear alkanes having 7 to 18, preferably 7 to 16, carbon atoms, e.g., n-heptane, n-nonane, n-decane, n-pentadecane, and the like.

(8) Esters and amides, including ethyl acetate, methyl propionate, butyl acetate, dimethyl formamide, N,N-diethyl-3-methylbenzamide, dimethyl acetamide, hexamethylene lauramide, higher N,N-dimethylalkylamides such as N,N-dimethylhexanamide, N,N-dimethyloctanamide, N,N-dimethyldecanamide, N,N-dimethyldodecanamide, N,N-dimethyldodecademide, and dimethyl lauramide.

(9) Pyrrolidones: A number of pyrrolidones are useful as barrier-modifying agents herein, and include, by way of example, 2-pyrrolidone, N-methyl-2-pyrrolidone, 5-methyl-2-pyrrolidone, N-ethyl-2-pyrrolidone, 1,5-dimethyl-2-pyrrolidone, N-hexyl-2-pyrrolidone, N-benzyl-2-pyrrolidone, N-phenyl-2-pyrrolidone, N-lauryl-2-pyrrolidone, 4-carboxy-N-methyl-2-pyrrolidone, 4-carboxy-N-hexyl-2-pyrrolidone, 4-carboxy-N-lauryl-2-pyrrolidone, 4-methoxycarbonyl-N-methyl-2-pyrrolidone, 4-methoxycarbonyl-N-hexyl-2-pyrrolidone, 4-methoxycarbonyl-N-lauryl-2-pyrrolidone, 2-pyrrolidone-5-carboxylic acid (pyroglutamic acid) and the decyl, oleyl and dodecyl esters thereof, N-farnesyl-2-pyrrolidone, 3-hydroxy-N-methyl-2-pyrrolidone, methylthioethyl pyrrolidone, 1-[2-(decylthio)ethyl]azacyclopentan-2-one (pirotiodecane), 2-mercaptoethylpyrrolidone, 1-dodecyl-2-pyrrolidone, and 3-dodecyl-2-pyrrolidone.

(10) Sulfoxides: Exemplary sulfoxides that can serve as barrier modifiers include, but are not limited to, dimethylsulfoxide (DMSO), decyl methylsulfoxide ($C_{10}$MSO), and the 2-alkyl-(tetrahydrothiophene)-1-oxides.

(11) Cyclodextrins include, without limitation, α-cyclodextrin, β-cyclodextrin, γ-cyclodextrin, 2-hydroxypropyl-β-cyclodextrin, 2,6-dimethyl-β-cyclodextrin, β-cyclodextrin-epichlorohydrin polymer, carboxymethylethyl-β-cyclodextrin, diethyl-β-cyclodextrin, and triethyl-β-cyclodextrin.

(12) Alkyl N,N-Disubstituted Amino esters: These include dodecyl-N,N-dimethylamino acetate, dodecyl 2-(N,N)-dimethylamino propionate, and the like.

(13) N-Alkyl-Azacycloalkanones and N-alkyl-azacycloalkenones: These include 1-hexyl azacycloheptan-2-one, 1-octyl azacycloheptan-2-one, 1-decyl azacycloheptan-2-one, 1-dodecyl azacycloheptan-2-one (laurocapram; Azone®), 1-tetradecyl azacycloheptan-2-one, 1-hexadecyl azacycloheptan-2-one, 1-geranyl azacycloheptan-2-one, 1-farnesyl azacycloheptan-2-one, 1-geranylgeranylazacycloheptan-2-one, 1-(3,7-dimethyloctyl)azacycloheptan-2-one, 1-(3,7,11-trimethyldodecyl)azacycloheptan-2-one, 1-geranyl azacyclohexan-2-one, 1-geranylgeranylazacyclohexan-2-one, 1-geranyl azacyclopentan-2,5-dione, 1-farnesyl azacyclopentan-2-one, 1-n-dodecylazacyclohept-3-ene-2-one, 1-n-dodecylazacyclohept-4-ene-2-one, 1-n-dodecanoyl-3-methylazacyclohept-3-ene-2one, and 1-n-dodecanoylazacyclohept-4-ene-2-one.

(14) Urea and its Derivatives, including 1-dodecylurea, 1,3-didodecylurea, and 1,3-diphenylurea.

(15) Terpenes are hydrocarbons that contain isoprene ($C_5H_8$) units, and, as such, include, without limitation, α-pinene, d-limonene, 3-carene, α-terpinenol, terpinen-4-ol, carveol, menthol, carvone, piperitone, pulegone, menthone, limonene oxide, pinene oxide, ascaridole, and 1,8-cineole.

The barrier-modifying agents will be present in the range of approximately 0.1 to 50%, more preferably in the range of approximately 0.5 to 40%, and most preferably in the range of approximately 1.0 to 10% (v/v) in the formulation delivered to the skin from a reservoir contained within a suitable iontophoresis device.

IV. Implementation

A common feature of the various methods described herein is the use of an AC signal in conjunction with a barrier-modifying agent to maintain a substantially constant electrical state, so as to limit flux variability in the transport of compounds across a tissue such as a body surface. The electrical state is typically maintained throughout the time period during which transport occurs. By maintaining a substantially constant electrical state as well as a substantially constant state of electroporation, the effective pore charge density and pore size remain essentially constant during a treatment procedure. This in turn allows for a substantially constant, controllable and determinable transport rate for the agent being delivered. The administration of a barrier-modifying agent allows for the substantially constant electrical state and state of electroporation to be maintained using lower level of current, thereby increasing battery life and increasing patent comfort.

As used herein, the term "AC signal" generally refers to an electric signal (e.g., current or voltage) that reverses direction periodically. As described further below, typically the AC signal has a frequency of at least about 1 Hz. It should be understood that an AC signal refers not only to signals that reverse direction relative to a zero reference point, but also to signals that are biased relative to a zero reference point. The phrase "electrical state" refers to a state that correlates with or is a measure of the permeability of the tissue in the region being electroporated and that can be measured as an electrical value. A substantially constant electrical state correlates with a substantially constant electroporative state. A substantially constant electrical state is evidenced, for example, by a substantially constant resistance or conductance within the region being electroporated, and/or by a substantially constant transference number (fraction of total current carried by a particular agent) for the agent being transferred.

The methods can be used for the controlled and predictable delivery or extraction of various compounds, including both charged and uncharged species. As is typical in iontophoresis, the permeant primarily tends to be a charged entity. However, the present invention is not limited to the delivery of charged molecules. The methods set forth herein can be used in the delivery and extraction of uncharged agents as well.

The methods are designed to accomplish delivery of a composition of interest across a body tissue and more specifically across a localized region of body tissue. As used herein a "tissue" is defined to mean an aggregation of similar cells and/or cell components united in performance of a particular function. The tissue can be part of a living organism, a section excised from a living organism, or artificial. An artificial tissue is one in which an aggregation of cells are grown to function similar to a tissue in a living organism. The aggregated cells, however, are not obtained from a host (i.e., a living organism). Artificial tissues can be grown in vivo or in vitro. Human skin, for instance, can be cultured in vitro to obtain an aggregation of cells, of monolayer thickness or greater, that can function as a skin tissue in culture or once grafted onto a living host. Certain types of artificial tissues that can be utilized with certain methods of the invention are discussed, for example, in U.S. Pat. Nos. 4,458,678, 4,485,096, and 4,304,866.

Certain methods are performed with human or animal tissue. Thus, the invention may be used in various clinical applications for human patients, as well as veterinary applications. In the latter context, the invention may be used with any animal having body tissues in which pores can be generated via the application of an electrical signal. Hence, some methods can be performed, for example, with domestic animals such as dogs and cats; farm animals such as horses, cows, sheep and pigs; exotic animals; birds; reptiles; and amphibians, or tissues from these animals. Still other methods are performed with plants or plant cell cultures.

A. The Ac Signal

Certain features of the applied AC signal assist in achieving the goal of maintaining a substantially constant electrical state while avoiding some of the problems associated with DC-based methods. For example, a problem with existing DC transdermal iontophoresis technology is that such methods allow skin resistance to vary over time; this in turn results in a variation in the delivery or transport rate of agents through the tissue. The use of an AC signal, however, can reduce this problem. Because the AC component continuously reverses polarity, the tissue remains substantially depolarized throughout the transport procedure and thus is less susceptible to building up charges that may continuously alter the skin structure and interfere with iontophoretic transport.

The AC signal also acts to facilitate transport by inducing the formation of new pores and/or enlarging the existing pores. It has been found by the present inventors that application of an AC signal can generate new pores in tissue without a concomitant enhancement of transport via electroosmosis. Thus, enhanced transport upon application of an AC signal is a consequence, at least in part, of new pore generation. (See, e.g., Li, et al. (1999) *J. Pharmaceutical Sciences* 88:419–427, which is incorporated herein by reference). By generating new pores, application of the AC signal can significantly enhance the rate of transport compared with passive diffusion alone.

Further, while many individuals skilled in the art believe that a DC field is required to transport a charged compound and that an AC signal lacks the necessary driving force for iontophoretic transport, the present inventors have discovered that AC iontophoresis does not eliminate the direct-field effect (i.e., electrophoresis) and about 10% of this effect remains at a relatively low frequency AC (e.g., 10 Hz to 1 kHz). While not intending to be bound by any particular theory, this AC flux-enhancing phenomena is thought to be a result of asymmetric boundary conditions of the agent across the skin. Thus, an AC signal also provides a means to enhance transport via the reduced direct field effect and electroporation without complications from the electrochemical reactions of the electrodes (e.g. water hydrolysis).

There are other benefits that can be obtained from utilization of an AC signal beyond the enhanced level of controlled delivery. For instance, application of an AC signal during transport, compared to traditional DC iontophoresis, causes less skin irritation and has a higher threshold of sensation. The use of a barrier-modifying agent in conjunction with the AC signal further reduces skin irritation. It has been shown that the threshold current for sensation is higher at high AC frequency than for DC. Thus, an AC field for new pore induction in skin during iontophoresis is better than DC for these issues, particularly when enhanced by the application of a barrier-modifying agent (See, e.g., Dalziel and Mansfield, AIEE Trans, Volume 69, Year 1950, Pages 1162–1168; and Dalziel and Massoglia, AIEE Trans, Volume 75, Year 1956, Pages 49–56).

These frequency relationships are important for another reason. Results on the frequency effects upon the extent of pore induction in skin show very small dependency of frequency on the extent of pore formation in the low AC frequency region (e.g., 10 to 250 Hz). This result indicates that the effect of frequency upon pore induction in skin is less than those upon the thresholds of sensation. Therefore, an optimal AC frequency region can be utilized in AC methods in which a high AC voltage is employed to increase the extent of pore induction and to enhance transport with minimal sensation and irritation.

As described in greater detail below, application of the AC signal (and optional prepulse and DC offset signal) is typically applied to a tissue using at least one pair of electrodes that are placed in contact with the tissue being treated. The barrier-modifying agent may be pre-applied to the tissue or maybe applied concurrently with the AC signal. At least one electrode includes a reservoir that contains the agent (e.g., a pharmaceutical agent) that is to be delivered or is capable of receiving the substance (e.g., metabolite) that is to be extracted. This electrode is positioned over the region of the tissue through which transport is to occur. A second electrode is also placed in contact with the tissue and is positioned to form a complete electric circuit with a current source. The AC signal can be applied with or without excipients that optimize the conditions for transport of agent(s) across the tissue.

For methods performed with humans, the electrodes are often placed in contact with the outermost skin layer, the stratum corneum. Application of the AC signal, combined with an optional prepulse signal, generates and maintains pores within the skin, thereby allowing agent(s) to be transported across the stratum corneum and into the dermo-epidermal layer.

The applied AC signal is of an appropriate voltage and waveform to effectively induce and/or maintain a desired electrical state, which state is an electroporated state that allows for enhanced transport of the agent relative to untreated tissue. Typically, the target electrical state is a selected electrical resistance or electrical conductance. The presence of the barrier-modifying agent allows for the selected electrical resistance to be achieved using a reduced level of current or voltage difference. Alternatively, or in addition, other electrical parameters from which electrical resistance or conductance values can be determined can be monitored, as well as any other parameters that correspond to the degree of tissue permeability. Typically, the AC signal is applied to maintain the substantially constant electrical state throughout the time period during which transport of agent is occurring. The actual period for delivery varies significantly depending upon the nature of the application. Some applications can be performed in less than 10 minutes, while other applications may last 12 hours to 24 hours or more.

During the treatment, the AC signal is varied as needed to maintain the electrical state at a selected target value, or more typically, within a target range. Most typically this is achieved by varying the amplitude and/or frequency of the applied voltage. For methods in which electrical resistance of a patient's skin is monitored, the target resistance may vary somewhat from individual to individual. In general, however, the target resistance tends to be approximately 1–30 k$\Omega$ cm$^2$, and more typically a value within the range of 5–15 k$\Omega$ cm$^2$. Generally, the barrier-modifying agent decreases the time to reach a target resistance level, e.g., 5 k$\Omega$, by at least 20%, preferably by at least 50%, and most preferably by at least 70%.

The AC signal is typically applied as necessary to maintain the selected target value such that the measured value does not increase or decrease by more than about 20% of the target value. Thus, if the target is 5 k$\Omega$ cm$^2$, then the AC signal is varied as required to keep the measured resistance within the range of about 4–6 k$\Omega$ cm$^2$. In certain other methods, the fluctuation is limited to less than 10% of the target value, in other methods, less than about 5%, and in still other methods, less than about 1%.

The frequency, waveform and duration of the AC signal can vary as long as it is effective to maintain the selected electrical state within the desired range. In general, however, the frequency of the AC signal tends to be at least about 1 Hz. In certain methods, the applied frequency generally falls within the range of about 1 Hz to about 1 kHz; while in other methods, the frequency usually is within the range of about 1 kHz to about 10 kHz. In yet other methods, the frequency usually is within the range of 10 kHz to 30 kHz, or 30 kHz to 200 kHz. The actual frequency can be any particular value or range of values within these ranges. A variety of waveforms can be utilized. Suitable waveforms include both symmetric and asymmetric waveforms, including waveforms having square, triangular, sinusoidal, saw-tooth and trapezoidal shapes and the like.

The size of the region of the tissue to which a signal is applied can vary significantly depending upon the nature of the application. In general, the region being electroporated and through which the agent is transported or compound is extracted tends to be from less than 1 cm$^2$ to greater than about 200 cm$^2$. The size of the region tends to be smaller in other applications, ranging from about 5 cm$^2$ to greater than 100 cm$^2$. In still other methods, the region tends to be about 5 cm$^2$ to about 30 cm$^2$. The size of the region can also be any particular value within these ranges. The shape of the region can be any geometric shape and is not limited to any one particular shape or type of shape.

Some methods utilizing AC signals to effect transport without a DC component can be useful for driving or extracting an electronically neutral agent or compound across a tissue. The inventors of the present invention have also found that methods conducted using AC signals at frequencies above about 1 Hz without the application of DC involve little or no electroosmosis. Thus, when performing delivery utilizing only an AC signal, there is negligible electroosmosis. Furthermore, when transporting an electronically neutral agent, there is no electrophoresis. Transport in this situation is similar to passive diffusion but is enhanced due to the induction of new pores (i.e., higher skin porosity) and/or enlarged or increased porosity due to electroporation. Although transport of neutral agents under AC can result in lower fluxes than with traditional constant current DC systems (due mostly to the absence of electroosmosis), methods using strictly AC signals are nonetheless useful because intra-patient and inter-patient variability associated with variable pore surface charge density is minimized. Additionally, there is no electrostatic partitioning of agents into the skin for neutral permeants.

B. Optional Prepulse

As explained in International Patent Publication Nos. WO 01/60448 and WO 01/60449, a relatively high-voltage DC or AC prepulse can optionally be applied to the body tissue to quickly attain a target electrical state or state of electroporation which is subsequently maintained by adjusting the AC signal. The use of a barrier-modifying agent allows a reduced voltage DC or AC prepulse to be used to attain the target electrical state relative to the voltage required when a barrier-modifying agent is not applied. Once the prepulse elicits the desired electrical state, the flux of the compound being delivered can be controlled by maintaining a substantially constant electrical state within the electroporated region (e.g., a substantially constant resistance or conductance). When an AC signal is utilized as a prepulse, this signal can subsequently be utilized to maintain the target electrical state. The AC prepulse can also be followed with a separate AC signal to maintain the target electrical state, typically applied shortly after completion of the prepulse.

While the AC signal and barrier-modifying agent alone can be used to reach the desired electrical state, the advantage of using a prepulse is that it can accelerate the process of establishing the target electrical state. The longer time period associated with using strictly an AC signal and barrier-modifying agent alone without a prepulse, however, is still preferable over a DC-only protocol since the AC-only protocol still results in a predictable and stable electrical state that promotes constant transport properties for the tissue, which is not the case when applying DC signals alone.

In general, the characteristics of the AC or DC prepulse are selected to be effective to obtain the desired electrical state. Typically, this means that the prepulse signal is applied to reach a target electrical resistance or conductance. In the absence of a barrier-modifying agent, the required voltage of the prepulse could be as high as 90 V. See WO 01/60448 and WO 01/60449, cited supra. With the barrier-modifying agent, however, the required voltage is reduced by at least 20%, preferably by at least 50%, and most preferably by at least 70%. Typically, this means that the required voltage will be in the range of about 1 V to about 75 V, in some instances in the range of about 1 V to about 45 V, preferably in the range of about 1 V to about 10 V. If an AC prepulse is utilized, the AC prepulse can be symmetric or asymmetric. A variety of suitable AC prepulse waveforms can be used, including, but not limited to, a square waveform, a sinusoidal waveform, a saw-tooth waveform, a trapezoidal waveform. The duration of the prepulse is sufficiently long so as to achieve the target electrical state. Duration of the prepulse depends in part upon the voltage of the prepulse. In general, however, the prepulse is typically from less than 1 minute to more than 20 minutes. If a DC prepulse is utilized, it too can be supplied in a variety of waveforms wherein the shape is square, triangular, trapezoidal or saw-tooth, for example. As with an AC prepulse, the prepulse is of sufficient duration to establish the target electrical state.

C. Optional Dc Offset

Methods employing an AC signal alone to conduct transport across a tissue or extraction from a tissue involve primarily passive diffusion to achieve transport. As indicated above, however, and as described in WO 01/60448 and WO 01/60449, transport and extraction are improved over purely passive transport because the AC signal induces electroporation through which an agent or compound can passively diffuse. In addition, the existence of a small direct-field effect associated with AC protocols further enhances the transport or extraction of ionic compounds. To promote delivery or extraction and to accelerate the delivery or extraction process, the AC signal can optionally be combined with a DC offset signal. Methods utilizing this combination are sometimes referred to as an "AC plus DC protocol." With this particular combination of signals, the AC signal is utilized primarily to maintain a region of the tissue at a substantially constant electrical state to maintain a level of permeability that enhances transport. The DC offset signal is applied to assist in driving transport or extraction of the agent or compound. With such a combination of signals, a stable flux of agent or compound across the tissue can be achieved. This result contrasts with conventional methods using only DC signals to effectuate transport or extraction in which the flux of agent is often unpredictable and changes with the course of the treatment.

As a general matter, the DC offset signal applied to the tissue is typically effective to maintain a substantially constant rate of delivery or extraction of the agent being transferred across the tissue. Thus, the timing and duration of the DC offset signal in general is governed by this goal. The rate at which agent is delivered can be controlled by the electrical resistance or conductance of the tissue and the DC offset voltage or current. The barrier-modifying agent allows for a desired rate to be maintained using a lower DC offset voltage or current.

The DC offset signal is often applied essentially simultaneously with application of the AC signal. This timing is appropriate, for example, when a prepulse has already established the desired electrical state. In other methods, however, the DC offset signal is delayed until after the AC signal has been initiated. A delay may be appropriate, for instance, with methods conducted without a prepulse to allow the AC signal to establish the target electrical state. Normally, the voltage of the DC offset signal is in the range of about 0.1 V to about 5 V, while in other methods the voltage is in the range of about 0.1 to about 2.5 V. The current range typically is about 0.01 to 0.5 mA/cm$^2$.

D. Exemplary Methods

The foregoing parameters can be implemented in various combinations to yield a variety of different protocols for iontophoretically administering or extracting a compound of interest across a localized region of body tissue. Exemplary methods follow. While the methods can be conducted with a number of different tissue types, and different parameters can be monitored to assess the electrical state of the tissue, often such methods are performed with human tissue and involve monitoring the electrical resistance or conductance of the skin prior to and during iontophoresis.

1. AC-Only Protocol—Delivery

FIG. 1 illustrates a method (50) that begins with the selection (52) of a target electrical value or range (e.g., skin resistance or conductance). As indicated supra, the particular target selected can vary somewhat depending upon the individual being treated and the nature of the compound being delivered. A barrier-modifying agent (53) is applied followed by an AC signal (54) to reach the desired target electrical state and to facilitate delivery of the compound across the tissue. As indicated above, application of an AC signal alone without a prepulse may require a longer period of time to reach the desired target. Nonetheless, application of the AC signal significantly increases transport over simple passive diffusion for the reasons discussed supra. Moreover, by continually reversing polarity, the AC signal keeps the tissue depolarized and less susceptible to buildup of charged species at the surface of the tissue. The AC signal also maintains a relatively constant level of skin permeability that allows for relatively constant, controlled and predictable delivery of the agent through the tissue.

During the time that the AC signal is applied, the electrical state of the tissue is measured (58), either continuously or periodically, to determine whether the electrical state of the tissue remains within the target range. If the electrical state is within the target range, the AC signals are applied without modification. If, however, the measured electrical state drifts outside the target range, then the AC signal is adjusted (60) to return the electrical state back within the target range. The AC signal is applied for a period sufficient to deliver (56) the desired amount of agent across the tissue at a substantially constant rate. Once the delivery period is complete (56), the treatment ends (62).

2. AC-Only Protocol—Extraction

Figure 2:
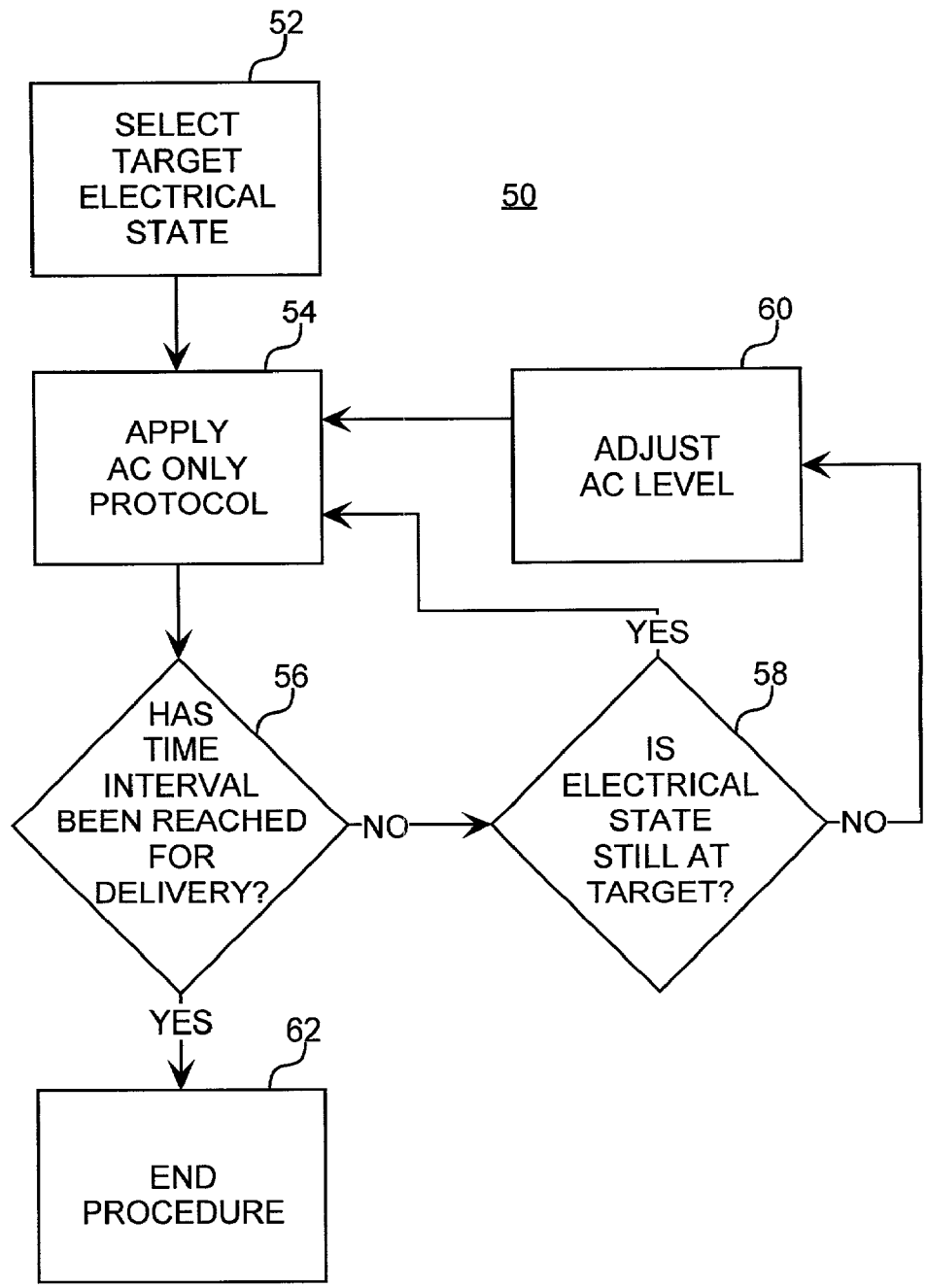
FIG. 2 is a schematic block diagram illustrating steps in a method utilizing only an AC signal to extract a compound of interest from beneath a patient's body surface as provided herein.

FIG. 2 illustrates a method (50) that begins with the selection (52) of a target value or range (e.g., target skin resistance or conductance). As indicated above, the particular target selected can vary depending upon the individual being treated and the nature of the substance being extracted. A barrier-modifying agent (53) is applied followed by an AC signal (54) to reach the desired target electrical state and to facilitate extraction of the substance across the tissue. As indicated above, application of an AC signal alone, without a prepulse, may require a longer period to reach the desired target. Nonetheless, application of the AC signal significantly increases transport over simple passive diffusion, as pointed out earlier herein. Moreover, the AC signal, by virtue of the continual reversal of polarity, keeps the tissue depolarized and less susceptible to buildup of charged species at the surface of the tissue. The AC signal also maintains a relatively constant level of skin permeability that allows for relatively constant, controlled, predictable, and determinable extraction of a compound through the localized region of body tissue.

During the time period in which the AC signal is applied, the electrical state of the tissue is measured (58), either continuously or periodically, to determine whether the electrical state of the tissue remains within the target range. If the electrical state is within the target range, the AC signals are applied without modification. If, however, the measured electrical state drifts outside the target range, then the AC signal is adjusted (60) to return the electrical state back within the target range. The AC signal is applied for a period sufficient to extract 56 the desired amount of substance across the tissue at a substantially constant rate after which the method ends (62).

3. AC Plus Prepulse Protocol—Delivery

Figure 3:
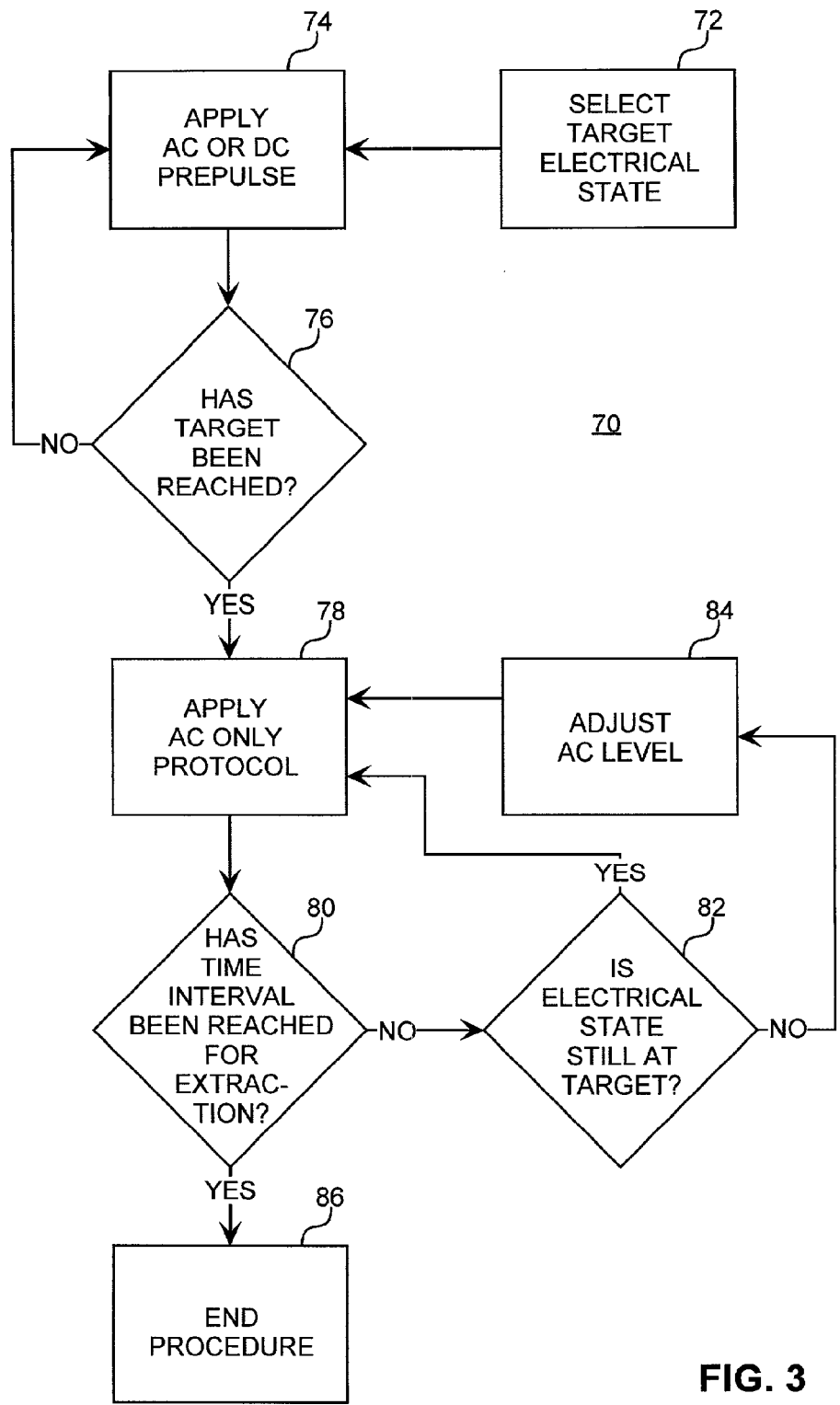
FIG. 3 is a schematic block diagram illustrating steps in a method utilizing an AC signal and a prepulse to transport a compound of interest across a localized region of body tissue as provided herein.

A schematic illustration of one AC-plus-prepulse method (70) is set forth in FIG. 3. With this particular approach, the selection 72 of a target electrical state is as described for the AC-only protocol delivery and shown in FIG. 1. However, prior to application (78) of the AC signal, a barrier modifying agent and an AC or a DC prepulse is applied (74) to the tissue to relatively quickly achieve the selected electrical state. Once it has been determined that the target state has been reached (76), an AC signal is applied (78) to the tissue. The electrical state is monitored (82) continuously or periodically as described in the preceding section to maintain the target electrical state throughout the time period during which delivery occurs. The AC signal is adjusted (84) as needed to maintain the target state. Once the delivery period is completed (80), the procedure ends (86).

4. AC Plus Prepulse Protocol—Extraction

Figure 4:
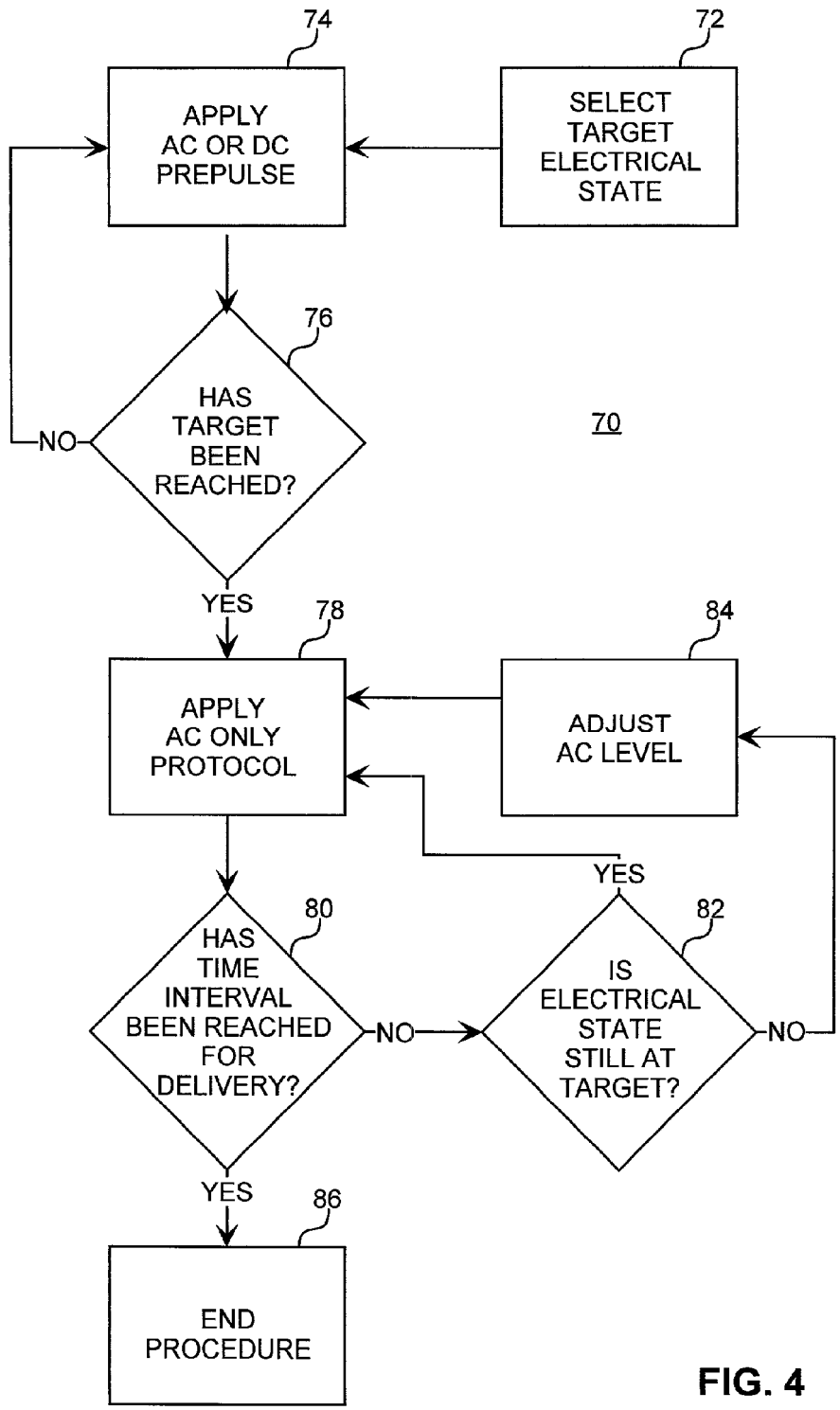
FIG. 4 is a schematic block diagram illustrating steps in a method utilizing an AC signal and a prepulse to extract compound of interest from beneath a patient's body surface as provided herein.

A schematic illustration of one AC plus prepulse method (70) is set forth in FIG. 4. With this particular approach, the selection (72) of a target electrical state is as described for the AC-only extraction protocol and shown in FIG. 2. However, prior to application (78) of the AC signal, a barrier modifying agent and an AC or a DC prepulse is applied (74) to the tissue to relatively quickly achieve the selected electrical state. Once it has been determined that the target state has been reached (76), an AC signal is applied (78) to the tissue. The electrical state is monitored (82) continuously or periodically as described in the preceding section to maintain the target electrical state throughout the time period during which extraction occurs. The AC signal is adjusted (84) as needed to maintain the target state. Once the extraction period is completed (80), the procedure ends (86).

5. AC Plus DC Offset—Delivery

Figure 5:
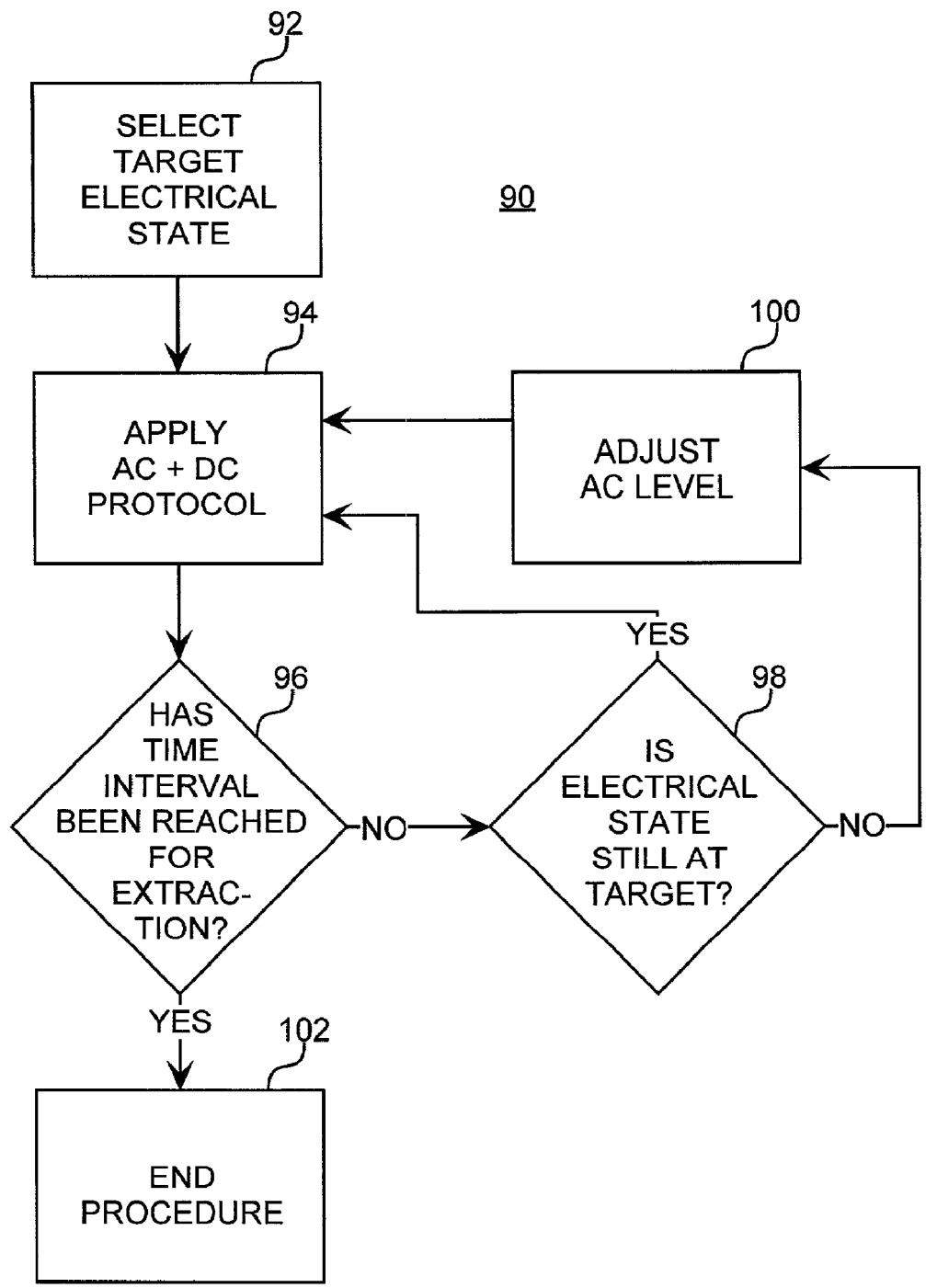
FIG. 5 is a schematic block diagram illustrating steps of a method utilizing an AC signal and a DC offset signal to transport a compound of interest across a localized region of body tissue as provided herein.

FIG. 5 illustrates the primary aspects of a method (90) utilizing an AC plus DC offset protocol. The initial stages of the method generally track those described for the AC-only protocol including selection (92) of a target electrical state. In this particular method, however, a barrier modifying agent and an AC signal and a DC offset signal are applied (94) to the tissue. The DC offset signal can be applied simultaneously with the application of the AC signal or at any time during the treatment. If it is determined (98) that the electrical state is no longer at the targeted value, the AC signal is adjusted (100) to return the electrical state to the target value or range. Such an adjustment is usually independent to the DC signal and does not affect the DC driven transport. The DC signal is typically kept constant but can optionally be adjusted during the application period (94) to change the delivery rate of the agent being transferred. Once a desired amount of agent has been delivered (96) or the time period of treatment has expired, application of the AC and DC signals is terminated (102).

6. AC Plus DC Offset—Extraction

Figure 6:
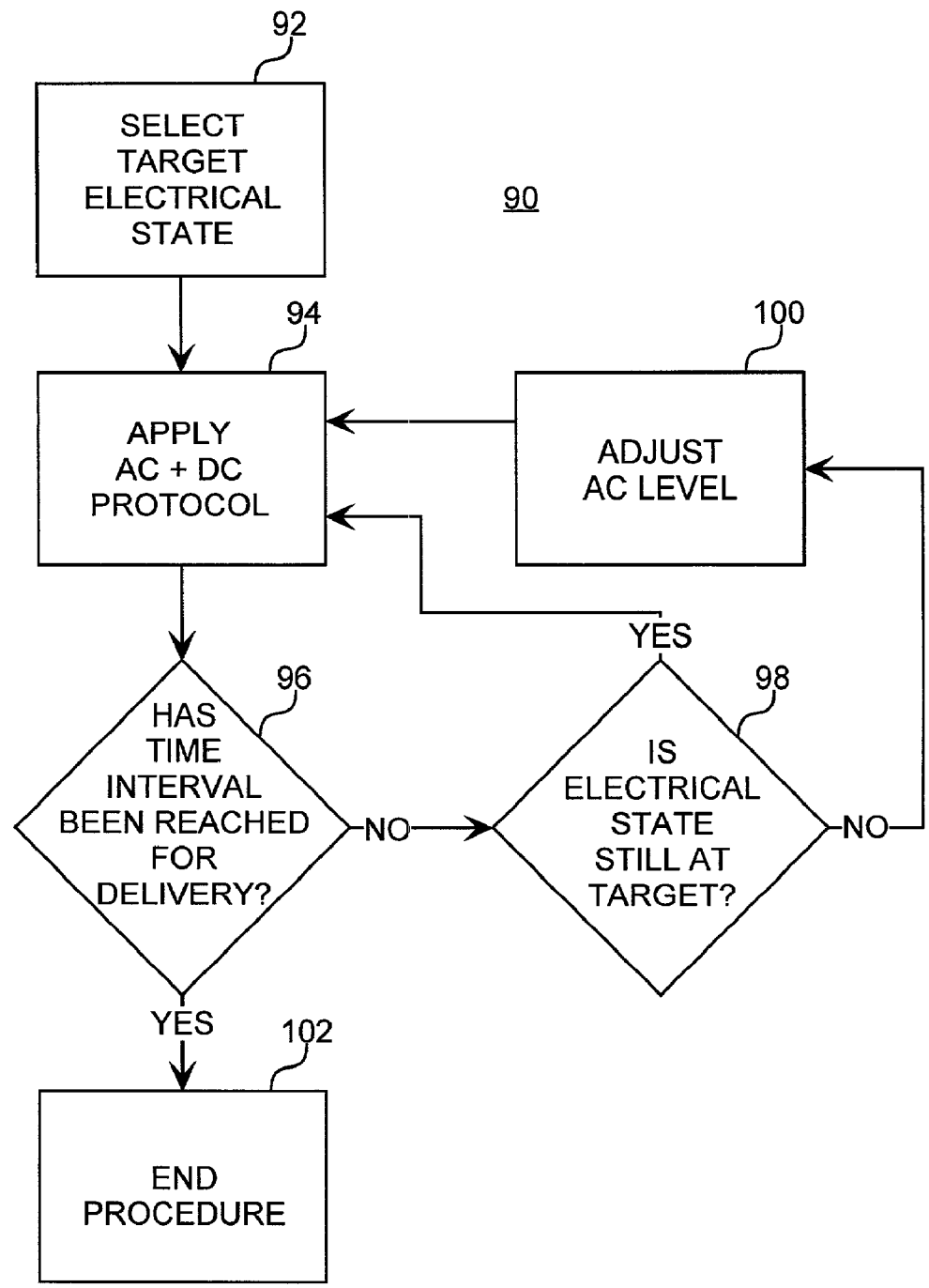
FIG. 6 is a schematic block diagram illustrating steps of a method utilizing an AC signal and a DC offset signal to extract a compound of interest from beneath a patient's body surface as provided herein.
Figure 7:
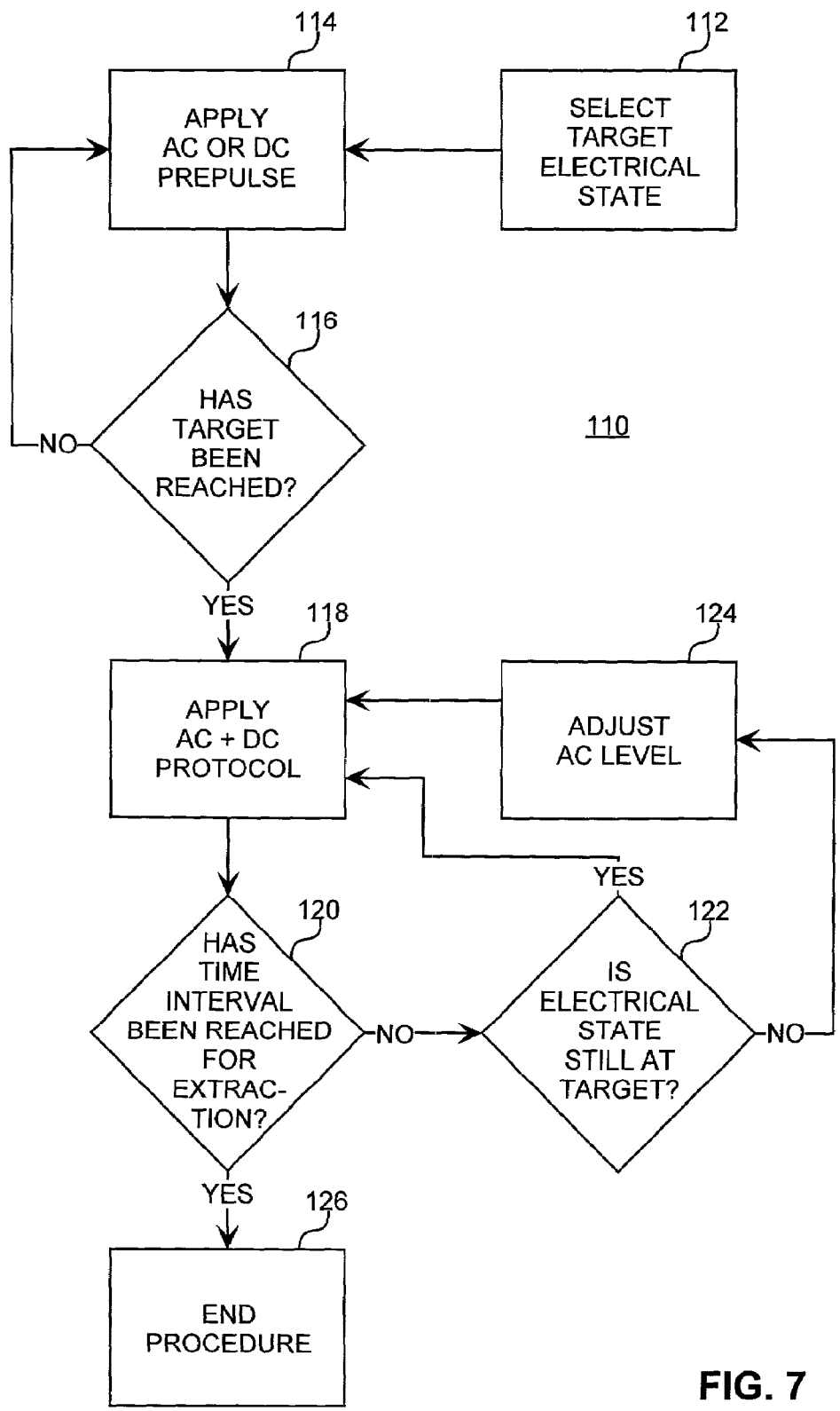
FIG. 7 is a schematic block diagram illustrating steps of one method utilizing a prepulse, an AC signal and a DC offset signal to transport a compound of interest across a localized region of body tissue as provided herein.

FIG. 6 illustrates the primary aspects of a method (90) utilizing an AC plus DC offset protocol. The initial stages of the method generally track those described for the AC-only protocol including selection (92) of a target electrical state. In this particular method, however, a barrier modifying agent and an AC signal and a DC offset signal are applied (94) to the tissue. The DC offset signal can be applied simultaneously with the application of the AC signal or any time during the treatment period. If it is determined (98) that the electrical state is no longer at the targeted value, the AC signal is adjusted (100) to return the electrical state to the target value or range. Such an adjustment is usually independent of the DC signal and is generally non-interfering with the DC driven transport. The DC signal is typically kept constant but can optionally be adjusted to change the extraction rate of the substance being transferred during the treatment. Once the desired amount of substance has been extracted (96), application of the AC and DC signals is terminated (102).

7. AC Plus Prepulse Plus DC Offset Delivery

Figure 8:
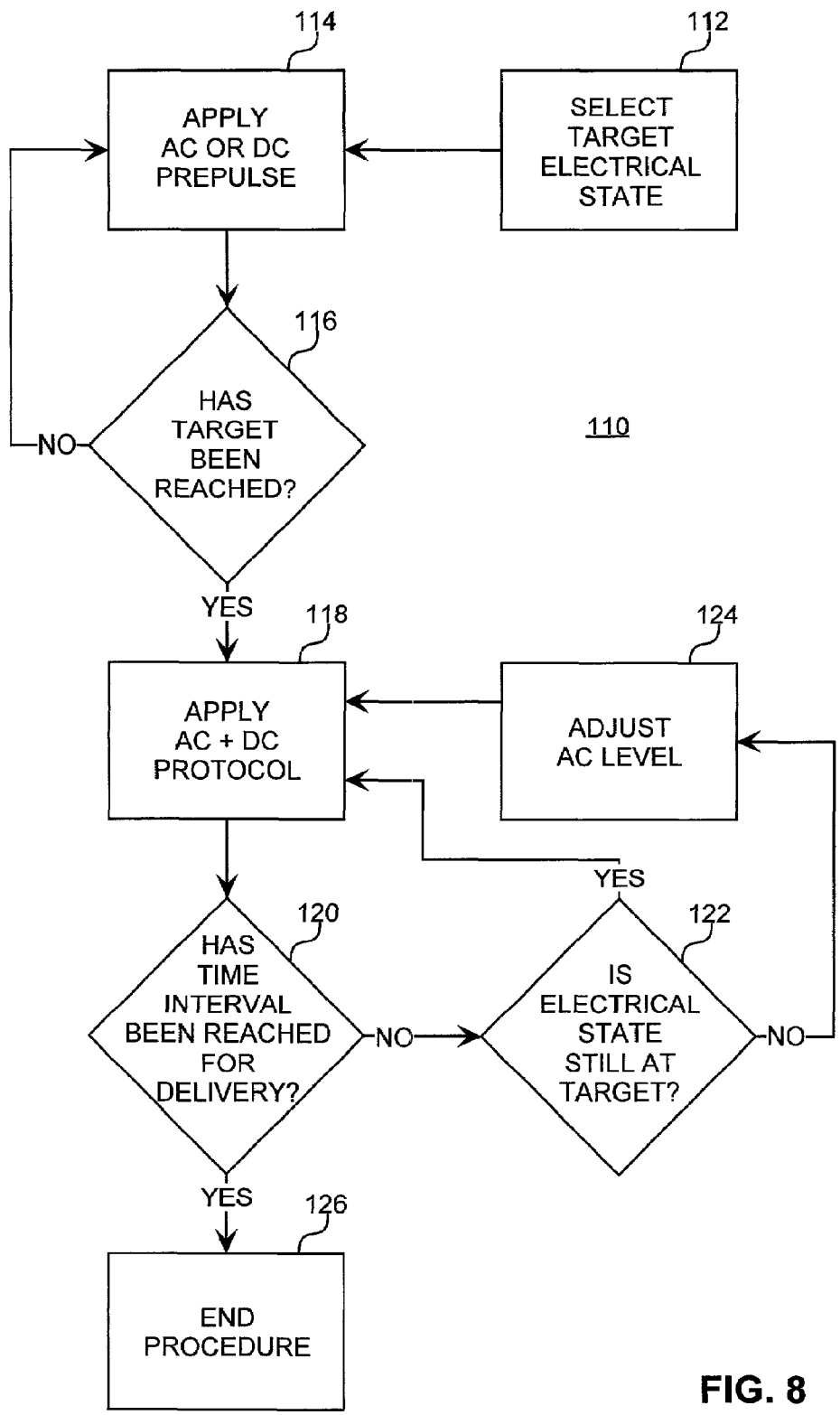
FIG. 8 is a schematic block diagram illustrating steps of one method utilizing a prepulse, an AC signal and a DC offset signal to extract a compound of interest from beneath a patient's body surface as provided herein.

Certain methods (110) combine the prepulse and the DC offset signals with the AC signal (see FIG. 8). Such methods utilize the unique features of each type of signal to optimize delivery of an agent. As described supra, a target electrical state is selected (112) followed by application (114) of a barrier-modifying agent and an AC or DC prepulse to quickly establish a selected electrical state correlated with an increased level of tissue permeability that promotes delivery of the agent. Once it is determined (116) that the target state has been reached, the AC signal and DC offset signal are applied (118), with the AC signal primarily functioning to maintain the target electrical state and the DC offset acting to promote transport of agent across the electroporated tissue. The electrical state is monitored (122). If the electrical state is found to vary from the target, the AC signal is adjusted (124) as required to return the electrical state to the target. Once the treatment time has elapsed (120), the process is completed (126).

8. AC Plus Prepulse Plus DC Offset Extraction

Certain methods (110) combine the prepulse and the DC offset signals with the AC signal (see FIG. 8). Such methods utilize the unique features of each type of signal to optimize extraction of a substance. As described supra, a target electrical state is selected (112) followed by application (114) of a barrier-modifying agent and an AC or DC prepulse to quickly establish a selected electrical state correlated with an increased level of tissue permeability that promotes extraction of the substance. Once it is determined (116) that the target state has been reached, the AC signal and DC offset signal are applied (118), with the AC signal primarily functioning to maintain the target electrical state and the DC offset acting to promote transport of substance across the electroporated tissue. The electrical state is monitored (122). If the electrical state is found to vary from the target, the AC signal is adjusted (124) as required to return the electrical state to the target. Once the desired amount of substance has been extracted (120), the process is completed (126).

E. Analytic Processes Following Extraction

The presence of a particular substance of interest in the reservoir can be detected utilizing a variety of techniques. For example, if a liquid is collected within the reservoir, the presence of one or more compounds of interest within the liquid can be detected using any of a variety of analytical techniques such as various chromatographic methods (e.g., high performance liquid chromatography [HPLC]), spectroscopic methods (e.g., infra-red spectroscopy [IR], nuclear magnetic resonance spectroscopy [NMR] and mass spectroscopy [MS]), electrochemical methods (e.g., electrical resistance and/or electrical potential), and enzymatic methods coupled with colorimetric analysis or electrical potential changes. Combinations of analytical techniques can also be utilized (e.g., gas chromatography/mass spectroscopy [GC/MS]). Detection of the substance can be either qualitative or quantitative.

The reservoir can include various agents that specifically react with one or more compounds of interest to form a detectable product or complex. For example, the reservoir can include a dye that emits or absorbs light of a particular wavelength upon interaction with a particular compound. Alternatively, an enzyme with specific activity for the analyte can be coupled to another enzyme with specific activity for another ligand capable of releasing electrons detectable by a sensor when metabolized by the second enzyme. For example, if the extracted substance is glucose, the enzyme can be glucose oxidase. The glucose oxidase can be coupled with peroxidases, which cause electron release that can be detected by a sensor. Various other sensors can be utilized to detect glucose, such as glucose selective electrodes (see, e.g., Solsky, R. L. (1988) *Anal. Chem.* 60:106R–113R) and various in situ analyses known in the art (e.g., calorimetric analyses).

The concentration of a substance in the extraction reservoir can be correlated with the concentration of the substance amount or concentration of the substance in the patient's body in various ways. In some instances, mathematical algorithms established from a large population set or calibration procedures are utilized to correlate the two values.

F. Analytes

The methods disclosed herein can be used in the extraction of a wide range of analytes, i.e., any substance that is in the system or body (e.g., circulating system, tissue system) of a patient and that can be transported across an electroporated tissue. When the tissue is human skin, the substance is either endogenous or one previously introduced into the body by some means. Thus, the extracted compounds, i.e., the analytes, can be molecular entities that are markers of disease states, pharmacologically active agents that have been administered to the subject, metabolites of such pharmacologically active agents, substances of abuse, electrolytes, minerals, hormones, peptides, metal ions, nucleic acids, genes, and enzymes or any metabolites, conjugates, prodrugs, analogs or other derivatives of the aforementioned substances. In some instances, more than one substance is monitored at a time. Specific monitoring applications are described infra. The substances can be charged (negatively or positively), uncharged or electronically neutral (e.g., zwitterionic substances with an equal number of opposite charges).

Substances that can be monitored further include, but are not limited to, oligosaccharides, monosaccharides (e.g., glucose), various organic acids (e.g., pyruvic acid and lactic acid), alcohols, fatty acids, cholesterol and cholesterol-based compounds, and amino acids. A number of different analytes that correlate with particular diseases or disease states can be monitored. For example, phenylalanine levels can be ascertained to monitor the treatment of phenylketonuria, a condition that is manifested by elevated blood phenylalanine levels. Examples of metal analytes that can be monitored include, but are not limited to, zinc, iron, copper, magnesium and potassium. Additional analytes that can be extracted from humans are discussed in "Iontophoresis Devices for Drug Delivery," by Praveen Tyle, Pharmaceutical Research, vol. 3, no. 6, pp. 318–326.

The present methodology can also be utilized to assess the concentration of various pharmacologically active agents that have been administered for either therapeutic or prophylactic treatment. Examples of such substances include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; antiinflammatory agents; antimigraine agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; Lagonist; tocolytic agents; and active metabolites thereof G. Drug Delivery The methods disclosed herein can be used in the transdermal or transmucosal delivery of a wide range of pharmacologically active agents. The methods can generally be utilized to deliver any active agent that can be iontophoretically transported across tissue. In general, a pharmacologically active agent that will be iontophoretically administered using the present method will be selected from the classes of active agents provided in the preceding section. In some methods, two or more pharmacologically active agents are administered in combination. Further, a pharmacologically active agent can be combined with various agents that enhance certain aspects of transport. For instance, a first active agent can be combined with a second active agent that improves blood circulation, to enhance the rate of delivery of the therapeutic agent throughout a patient's body. Other methods utilize one or more excipients that act to control the level of transport that occurs during the procedure.

The active agent will generally be delivered as a component of a pharmaceutical formulation suitable for topical, transdermal and/or transmucosal administration, and will contain at least one pharmaceutically acceptable vehicle. Examples of vehicles typically used in such formulations are distilled water, buffered water, physiological saline, PBS, Ringer's solution, dextrose solution, and Hank's solution. In addition, the formulation can include other carriers, adjuvants, and/or non-toxic, non-therapeutic, nonimmunogenic stabilizers, excipients and the like. The formulation may also include additional substances to approximate physiological conditions, such as pH adjusting and buffering agents, tonicity adjusting agents, wetting agents, detergents and the like. Further guidance regarding formulations that are suitable for various types of administration can be found in *Remington's Pharmaceutical Sciences*, Mack Publishing Company, Philadelphia, Pa., 17th ed. (1995).

The pharmacologically active agent delivered using the present methods is administered in an amount effective for prophylactic and/or therapeutic purposes. An effective therapeutic amount is an amount sufficient to remedy a disease state or symptoms, or otherwise prevent, hinder, retard, or reverse the progression of a disease or any other undesirable symptoms. An effective prophylactic amount is an amount sufficient to prevent, hinder or retard a disease or any other undesirable symptom. The effective amount of any particular active agent will depend upon a number of factors known to those of skill in the art, including, for example, the potency and potential toxicity of the agent, the stability of the agent in the body, and the age and weight of the patient.

The active agents can also be compounds that are not delivered for a therapeutic or prophylactic purpose, but that are otherwise physiologically or medically useful. Such compounds include, by way of example, nutrients and imaging agents.

V. Delivery Systems

Figure 9:
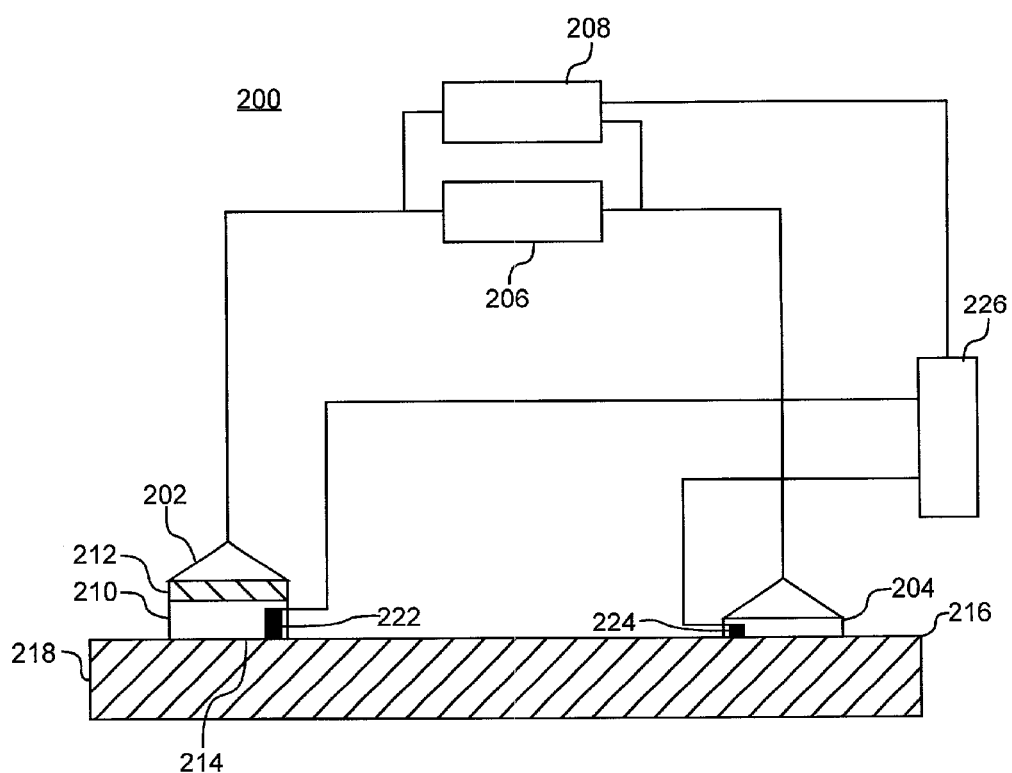
FIG. 9 is a schematic representation of an exemplary apparatus for iontophoretically delivering a pharmacologically active agent to a patient using the methodology of the invention.

One embodiment of an apparatus for performing the methods disclosed herein is represented schematically in FIG. 9. This system 200 for delivering agents across a tissue or body surface 218 generally comprises a first set of two electrodes 202, 204 electrically connected to a power source 206. The power source 206 can be a single source capable of delivering both an AC and a DC signal, or include two separate sources, one for delivering an AC signal and the other that delivers a DC signal. A circuit including the two electrodes 202, 204 and power source 206 is also connected to a controller 208 that monitors the electrical signals delivered to the electrodes 202, 204 and which can send signals to the power source 206 to alter the signals transmitted therefrom.

At least one of the electrodes 202 includes at least one reservoir (e.g., 210) and is electrically connected to a reservoir surface 212. Another surface 214 of the reservoir 210 is placed against a surface 216 of the tissue 218 (e.g., a patient's skin) and held in place, for example, by an adhesive or gel (not shown). If the barrier-modifying agent is to be applied concurrently with the AC signal, it may be housed within the reservoir 210 or placed on the reservoir surface 212. The reservoir 210 contains one or more agents (e.g., pharmaceutical agents) 220 that are to be delivered across the tissue 218. The reservoir 210 can be a chamber that houses a solution into which the agent(s) 220 is/are dissolved. Alternately, the reservoir 210 can include a porous material that retains a solution, paste or gel containing the agent(s) 220 to be delivered. Various other reservoir systems known to those of skill in the art can also be utilized. The other electrode 204 of the pair is also placed in contact with a surface 216 of the tissue 218 and held in position with an adhesive or gel (not shown). This electrode 204 is positioned to allow for formation of a current that flows between the two electrodes 202, 204. DC offset current can be applied to drive transport of a charged agent within the reservoir 210 across the tissue 218 toward the electrode of opposite charge. Uncharged agents are driven from the anode (the positive electrode) across the tissue 218 at physiological pH by electroosmosis.

The apparatus 200 includes a second set or monitoring set of electrodes 222, 224 that are placed within the region of the tissue being electroporated to monitor the electrical state of the tissue 218 during transport of the agent across the tissue. As indicated supra, the electrical state monitored is one that reflects the extent of tissue permeability or the state of electroporation (e.g., electrical resistance or electrical conductance). The monitoring electrodes 222, 224 can be separate from the first set of electrodes 202, 204, although this is not required, since the first set of electrodes 202, 204 can be used to monitor the electrical state of the tissue 218. The monitoring electrodes 222, 224 can be attached to a separate monitor 226 as shown in FIG. 5, or optionally to the same controller 208 as the first set of electrodes 202, 204. If attached to a separate monitor 226, monitor 226 can send signals regarding the electrical state of the tissue 218 as measured by the second set of electrodes 222, 224 to controller 208.

The first set of electrodes 202, 204 utilized in applying the electrical signals can be of any of the standard types of electrodes utilized in iontophoresis. Some systems use non-polarizable electrodes such as standard electrocardiograph electrodes manufactured from silver/silver chloride. Other suitable materials include gold, stainless steel and platinum. Multichannel dispersive electrodes can also be utilized in certain methods (see, e.g., U.S. Pat. No. 5,415,629).

When a DC offset signal is utilized, the electrode including the reservoir functions as either the cathode or anode depending upon the charge of the agent being delivered. In general, the anode receives the positive contribution of the DC offset signal, whereas the cathode receives the negative contribution of the DC offset signal. Consequently, if a DC offset signal is applied, positively charged ions are driven into the tissue at the anode and negatively charged ions are driven across the tissue at the cathode. At physiological pH, neutral agents are driven by electroosmosis into the tissue from the anode. When a DC offset is not utilized and only an AC signal is delivered, there is no formal anode or cathode.

In some systems, it can be useful to include a reservoir at both electrodes 202, 204. For example, if only an AC signal is applied, agent can be transported via diffusion from either reservoir. As described further infra, some methods using a DC offset involve reversing the direction of current flow at different time points. Reservoirs located at both electrodes 202, 204 can be useful in such methods because delivery can occur from both reservoirs depending upon the direction of the DC signal. Two reservoirs can also be utilized to good effect if two different agents of opposite charge are to be delivered. In such instances, differently charged agents are placed in separate reservoirs so that delivery can proceed simultaneously from both reservoirs. Both reservoirs can also be used to deliver the barrier-modifying agent.

In operation, the reservoir 210 is filled with a solution or matrix that includes the agent 220 to be transferred. If the reservoir 210 includes an absorbent material, this is soaked with a solution containing the agent or coated with a paste or gel containing the agent. Once the first set of electrodes 202, 204 has been properly positioned, an electrical signal is delivered to the first set of electrodes 202, 204 via the power supply 206. The particular signals delivered depend upon which of the protocols disclosed supra are utilized. In general, however, the various methods involve utilizing the power supply 206 to generate an AC signal of appropriate shape, duration, frequency and voltage to maintain a selected electrical state. If during the transport process, the electrical state deviates from the target electrical state as detected by the monitoring electrodes 222, 224, then the appropriate adjustments are made with the power supply 206 to vary the AC signal such that the electrical state is brought back to the target value or within the target range.

The controller 208 can be under microprocessor control. If the microprocessor-based controller determines on the basis of signals from the monitoring electrodes 222, 224 that the electrical state has deviated from the target, it can signal the power source 206 to alter the AC signal so as to return the electrical state to the desired target. Such a controller can also include a safety shut off if it is determined that the electrical state of a patient's skin, for example, has reached a potentially dangerous level.

For methods utilizing either an AC or a DC prepulse, a prepulse of appropriate frequency, voltage and duration is generated by the power source 206 that is effective to reach the target electrical state. The monitoring electrodes 222, 224 can be utilized during this process to follow the progress towards the desired electrical state. Once this state is achieved, a signal is sent to the controller 208 that terminates generation of the prepulse and then generates the AC signal and/or the DC offset for application to the tissue.

As indicated above, in some methods the concentration of the agent 220 within the reservoir 210 is sufficiently higher than that on the other side of the tissue such that agent is transported through the electroporated region via passive diffusion. More typically, however, the power supply 206 is also utilized to generate a DC offset signal. This current drives the transport of a charged agent towards the electrode having an opposite charge or a neutral agent from the anode to cathode via electroosmosis. In some procedures, the direction of the DC offset current flow can be reversed between the first set of electrodes to maximize the use of both electrodes and avoid the generation of unwanted ions/products in the electrodes.

Through the use of solid-state circuitry, the various foregoing elements such as signal delivering electrodes, power supply and reservoir can be included in a small, integrated device that can be conveniently worn by an individual without interfering with the individual's daily activities.

VI. Extraction Systems

Figure 10:
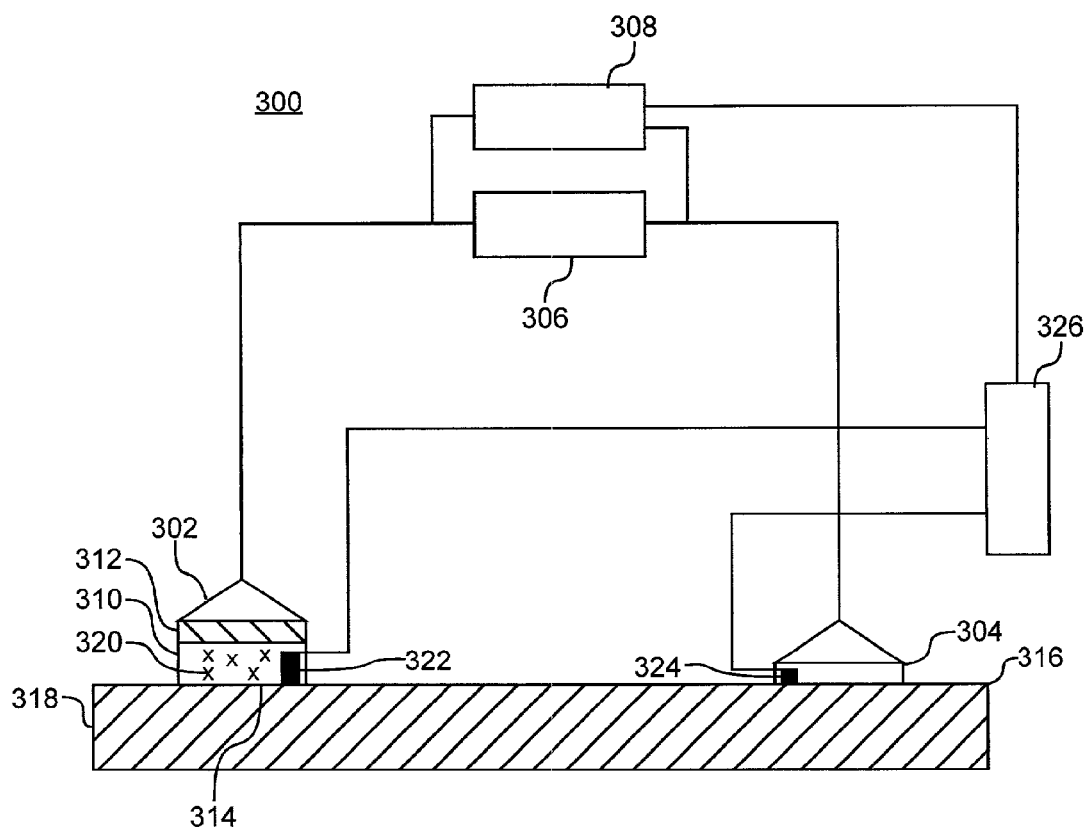
FIG. 10 is a schematic representation of an exemplary apparatus for iontophoretically extracting an analyte from beneath a patient's body surface, such as extracting a metabolite or pharmacologically active agent across the skin of a patient.

One embodiment of an apparatus for performing the methods disclosed herein is represented schematically in FIG. 10. This system 200 for extracting substances across a tissue or body surface 218 generally comprises a first set of two electrodes 202, 204 electrically connected to a power source 206. The power source 206 can be a single source capable of delivering both an AC and a DC signal, or include two separate sources, one for delivering an AC signal and the other that delivers a DC signal. A circuit including the two electrodes 202, 204 and power source 206 is also connected to a controller 208 that monitors the electrical signals delivered to the electrodes 202, 204 and which can send signals to the power source 206 to alter the signals transmitted therefrom.

At least one of the electrodes 202, 204 includes at least one reservoir (e.g., 210) and is electrically connected to a reservoir surface 212. Another surface 214 of the reservoir 210 is placed against a surface 216 of the tissue 218 (e.g., a patient's skin) and held in place, for example, by an adhesive or gel (not shown). The reservoir 210 is designed to receive one or more substances (e.g., metabolites or pharmaceutical agents, not shown) that are extracted across the tissue 218. If the barrier-modifying agent is to be applied concurrently with the AC signal, it may be housed within the reservoir 210 or placed on the reservoir surface 212. The other electrode 204 of the pair is also placed in contact with a surface 216 of the tissue 218 and held in position with an adhesive or gel (not shown). This electrode 204 is positioned to allow for formation of a current that flows between the two electrodes 202, 204. When only an AC signal is applied to the tissue 218, the direction of current flow changes direction between the two electrodes on a period equal to the frequency of the applied current. When a DC offset signal is applied using the electrodes 202, 204, current flow is in the direction to enhance the transport of a charged or uncharged substance within the system of the individual receiving treatment towards at least one reservoir across the tissue 218.

The apparatus 200 can optionally include a second set or monitoring set of electrodes 222, 224 that are placed within the region of the tissue being electroporated to monitor the electrical state of the tissue 218 during extraction of the substance across the tissue. As indicated supra, the electrical state monitored is one that reflects the extent of tissue permeability or the state of electroporation (e.g., electrical resistance or electrical conductance). This second set of electrodes is optional because the first set of electrodes 202, 204 can be used to monitor the electrical state of the tissue 218. The monitoring electrodes 222, 224 can be attached to a separate monitor 226 as shown in FIG. 10, or optionally to the same controller 208 as the first set of electrodes 202, 204. If attached to a separate monitor 226, monitor 226 can send signals regarding the electrical state of the tissue 218 as measured by the second set of electrodes 222, 224 to controller 208.

The first set of electrodes 202, 204 utilized in applying the electrical signals can be of any of the standard types of electrodes utilized in iontophoresis. Some systems use nonpolarizable electrodes such as standard electrocardiograph electrodes manufactured from silver/silver chloride. Other suitable materials include gold, stainless steel and platinum. Multichannel dispersive electrodes can also be utilized in certain methods (see, e.g., U.S. Pat. No. 5,415,629).

When a DC offset signal is utilized, the electrode including the reservoir functions as either the cathode or anode depending upon the charge of the substance being extracted. In general, the anode receives the positive contribution of the DC offset signal, whereas the cathode receives the negative contribution of the DC offset signal. Consequently, if a DC offset signal is applied, negatively charged ions are extracted through the tissue and received in the reservoir which is part of the anode; positively charged ions are extracted across the tissue and received in the reservoir which is part of the cathode. Because the direction of electroosmotic flow is from the anode to the cathode at physiological pH, uncharged substances are extracted across the tissue and received in the reservoir, which is part of the cathode. It should be noted that when a DC offset is not utilized and the signal only consists of AC, there is no formal anode or cathode.

In some systems, it can be useful to include a reservoir at both electrodes 202, 204. For example, if only an AC signal is applied, agent can be extracted via diffusion into either reservoir. As described further infra, some methods using a DC offset involve reversing the direction of current flow at different time points. Reservoirs located at both electrodes 202, 204 can be useful in such methods because extraction from the system of the individual into both reservoirs can occur depending upon the direction of the DC signal. Two reservoirs can also be utilized to good effect if two different substances of opposite charge, or if a neutral and a negatively charged substance, are to be extracted. In such instances, differently charged substances are extracted into separate reservoirs. Both reservoirs may also be used to contain the barrier-modifying agent.

In operation, the barrier-modifying agent may initially be applied to the region of tissue and then the first set of electrodes 202, 204 are positioned and then an electrical signal delivered to the first set of electrodes 202, 204 via the power supply 206. The particular signals delivered depend upon which of the protocols disclosed supra are utilized. As indicated above, however, the various methods generally involve utilizing the power supply 206 to generate an AC signal of appropriate shape, duration, frequency and voltage to maintain a selected electrical state. If during the transport process, the electrical state deviates from the target electrical state as detected by the monitoring electrodes 222, 224, then the appropriate adjustments are made with the power supply 206 to vary the AC signal such that the electrical state is brought back to the target value or within the target range.

The controller 208 can be under microprocessor control. If the microprocessor-based controller determines, on the basis of signals from the monitoring electrodes 222, 224, that the electrical state has deviated from the target, it can signal the power source 206 to alter the AC signal so as to return the electrical state to the desired target. Such a controller can also include a safety shut off if it is determined that the electrical state of a patient's skin, for example, has reached an unacceptable level.

For methods utilizing either an AC or a DC prepulse, a prepulse of appropriate frequency, voltage and duration is generated by the power source 206 that is effective to reach the target electrical state. The monitoring electrodes 222, 224 can be utilized during this process to follow the progress towards the desired electrical state. Once this state is achieved, a signal is sent to the controller 208, which terminates generation of the prepulse and then generates the AC signal and/or the DC offset for application to the tissue.

As indicated above, in some methods the concentration of the substance within the individual's system is sufficiently higher than that on the other side of the tissue such that agent is transported through the electroporated region via passive diffusion. More typically, however, the power supply 206 is also utilized to generate a DC offset signal. This current drives the transport of a charged substance towards the electrode having an opposite charge or an uncharged substance from anode to cathode. However, in some procedures, the direction of the DC current flow is reversed between the first set of electrodes in order to reduce potential skin irritation, prevent electrochemical depletion of the non-polarizable electrode, increase the surface area for extraction, and allow the biosensor to operate for longer periods of time.

Through the use of solid-state circuitry, the various foregoing elements such as signal extracting electrodes, power supply and reservoir can be included in a small, integrated device that can be conveniently worn by an individual without interfering with the individual's daily activities.

VII. Examplary Applications

The transport methods provided herein can be used in a variety of applications, including the treatment of various disorders and diseases. Certain methods are used in the treatment of diabetes and various weight disorders such as obesity, for example. In the treatment of diabetes, the methods can be used for the controlled delivery of insulin or other hypoglycemic agents, and in the administration of glucagon or other carbohydrates (e.g., glucose) to an individual who is hypoglycemic. Weight loss treatments can involve the delivery of appetite suppressors such as cholecystokinin, for example.

Related transport methods are performed to assist in treating individuals seeking to recover from narcotic or other types of substance abuse. These methods can involve, for example, the administration of agents that assist in the detoxification process. The delivery methods also find value in treating nicotine addiction. Treatment of nicotine addiction often involves a program in which decreasing levels of nicotine are delivered over an extended treatment period. Detoxification methods generally involve iontophoretic delivery of an agent that blocks the effect of, or substitutes for, the substance being abused.

Certain transport methods lend themselves well to the treatment of various blood circulation and pressure disorders. For example, the methods can be used in the iontophoretic delivery of various anticoagulants (e.g., heparin, low molecular weight heparin analogues, and warfarin sodium). Such methods can be useful in prevention of stroke and/or in the reducing clotting risk following certain surgical procedures. Treatment of blood pressure disorders is effected by the delivery of appropriate levels of blood pressure medicines, such as a-receptor blocking agents ("α-blockers") and □-receptor blocking agents ("□blockers"). The method of the invention is also useful in pain management, i.e., in the iontophoretiic delivery of various analgesic agents to control pain during surgery or in ongoing pain management. The method of the invention may also be used in the iontophoretic administration of drugs for treating psychiatric disorders, sleep disorders, movement disorders (e.g. Parkinson's disease), infections, and local and diffuse inflammatory disorders.

The present method is also useful in treating local rather than systemic conditions and disorders. For example, the method may be used to effect iontophoretic delivery of active agents appropriate for treating skin conditions such as acne, eczema and psoriasis, local inflammation, and the like. The invention may also be implemented in the fields of cosmetics and cosmeceuticals, for example, in hydrating the skin or in removing the external layer of the skin, thereby stimulating the activation of various collagen growth factors and the growth of new skin layers.

The extraction methods provided herein can also be used in a variety of applications, including the diagnosis and monitoring of various disorders and diseases, e.g., in monitoring a patient's glucose level on a periodic or substantially continuous basis. Instead of monitoring glucose levels directly, one can monitor a product formed during metabolism of glucose such as lactic acid and/or pyruvic acid. In addition, the method of the invention can be used to detect or monitor the presence of a substance within an individual's system that is correlated with a particular disease or disease state (i.e., a disease "marker"). As indicated above, phenylalanine levels can be monitored to assess risks for phenylketonuria, a disorder that is associated with elevated blood phenylalanine levels. Another example is the monitoring of blood alcohol or illicit substances as part of a court ordered treatment program.

The extraction methods also have utility in a variety of therapeutic applications. By way of example, the level of one or more pharmacologically active agents or metabolites thereof in a patient's body can be tracked as a way to assess the current levels of active agent within the patient's system and adjust dosage or dosing regimen, as necessary.

In yet a further embodiment, the tracking of a patient's blood level of a therapeutic agent can be coupled with a drug delivery device to automatically maintain the blood level of the active agent within a narrow therapeutic window. Thus, in such embodiments, certain systems of the invention, as described supra, can include a reservoir at one electrode for collecting the analyte extracted from the patient's body and a second reservoir at the second electrode for delivering the active agent. As a specific example, one iontophoretic system of the invention can be used both to extract glucose to monitor a patient's glucose level and to deliver insulin or another hypoglycemic agent as needed.

It is to be understood that while the invention has been described in conjunction with the preferred specific embodiments thereof, the foregoing description, as well as the example that follows, are intended to illustrate and not limit the scope of the invention. Other aspects, advantages, and modifications will be apparent to those skilled in the art to which the invention pertains. All patents, patent applications, journal articles, and other references cited herein are incorporated by reference in their entireties.

EXAMPLE

Materials

All of the experiments carried out below employed the upper half of a Franz-type diffusion cell (area~1 $cm^2$) held in place with a piece of double-sided foam adhesive (#4026 3M Corp., Minneapolis, Minn.) as housing for the iontophoretic electrode. AC electrical currents were produced with a custom-made current generator (EM-Tech Inc., Lindon, Utah).

Silver foil, silver chloride, isopropyl alcohol, and phosphate buffered saline tablets (0.01 M phosphate buffer, 0.0027 M potassium chloride and 0.137 M sodium chloride, pH 7.4 at 25° C. when one tablet is dissolved in 200 ml deionized water), were purchased from Sigma Chemical Co. (St. Louis, Mo.). Isopropyl myristate, sodium lauryl sulfate, and propylene glycol (all N.F. grade) were purchased from Spectrum Chemical (Gardena, Calif.), N.F. grade absolute ethanol from AARPER (Shelbyville, Ky.), and N.F. grade oleic acid from Mallinkrodt (Paris, Ky.). Ag paint was purchased from Ladd Research Industries (catalogue #60810, Williston, Vt.).

Electrodes: Silver foil was cleaned by thorough rubbing with 00 grade steel wool. Silver/Silver Chloride ink was prepared by mixing 1:1 (w/w) silver paint with finely ground silver chloride. The silver foil was then dipped in the Ag/AgCl mixture and allowed to cure at room temperature.

Oscilloscope: AC voltage was measured with a Kenwood model CS-6020 oscilloscope (Kenwood, Inc., Long Beach, Calif.). DC offset voltage was measured with a Fluke model 75-III Multimeter (Fluke Inc., Everett, Wash.).

AC voltage, with a constant 200 mV DC offset and a frequency of 500 Hz, was applied in an increasing magnitude until the test subject felt a strong, tingling sensation (typically≈30 V). The AC voltage was kept constant until a target resistance of 5 k$\Omega$ was achieved. When the target resistance was reached, the AC voltage was continually adjusted to maintain the target resistance. The AC voltage and time required to reach target resistance were recorded as raw data.

Time to Reach Target Resistance

Test subjects 1 and 4 responded readily to the electrical current, reaching a target resistance of 5 k$\Omega$ within minutes, even without application of a voltage-assisting agent. Subjects 2, 3, and 5, on the other hand, were not able to reach the target resistance within the 120-minute experiment without the aid of voltage assisting agent. Table 1 lists the time required for each subject to reach target resistance for each pretreatment condition.

TABLE 1

| Pretreatment | Time of Pretreatment | Treatment Code | Test Subject | | | | |
|---|---|---|---|---|---|---|---|
| | | | 1 | 2 | 3 | 4 | 5 |
| None | — | a | 10 | >120 | <1 | >120 | >120 |
| 95% ethanol in water | 1 hour | b | 3 | 50 | <1 | 80 | >120 |
| 95% ethanol in water | 3 hours | c | 10 | 15 | — | — | >120 |
| 5% oleic acid in ethanol | 1 hour | d | <1 | 20 | <1 | >120 | — |
| 5% oleic acid in ethanol | 3 hours | e | <1 | 15 | — | — | 45 |
| 1:1:1 oleic acid: isopropyl alcohol: propylene glycol | 3 hours | f | — | 20 | 50 | — | <1 |
| 1% sodium lauryl sulfate | 1 hour | g | 2 | — | 10 | — | — |
| 1% sodium lauryl sulfate | 3 hours | h | — | 4 | <1 | — | <1 |

Methodology

Five test subjects, four Caucasians and one of Asian descent, aged 25 to 36 years old, gave their informed consent to participate in the study. This study was conducted under approval of the University of Utah Health Sciences Institutional Review Board. This study was conducted at the University of Utah College of Pharmacy under a testing agreement between ACiont, Inc. (Salt Lake City, Utah) and the University of Utah Office of Sponsored Projects.

Each subject received iontophoresis without pretreatment and with some or all of the following pretreatments with a barrier-modifying agent(s):

1. 95% ethanol with 5% water (v/v)
2. 5% oleic acid in 95% ethanol (v/v)
3. 5% isopropyl myristate in 95% ethanol (v/v)
4. 1:1:1 oleic acid:isopropyl alcohol:propylene glycol (v/v/v)
5. 1% sodium lauryl sulfate in water (w/v)

Approximately 1.5 ml of the barrier-modifying agent was applied to a gauze pad (Curity Healthcare). The saturated gauze pad was covered with a piece of aluminum foil (Reynolds Aluminum) and then covered with an overlying piece of Tegaderm™ brand occlusive dressing (3M, Minneapolis, Minn.). The barrier-modifying agents were allowed to remain in contact with the skin from between one to three hours. Following removal of the patch, the skin was thoroughly wiped with an isopropyl alcohol swab (Curity Healthcare) and the top half of the Franz-type diffusion cell affixed to the treatment site. The Ag/AgCl electrodes were then inserted into the diffusion cell and the cell was filled with pH 7.4 phosphate buffered saline.

Figure 11:
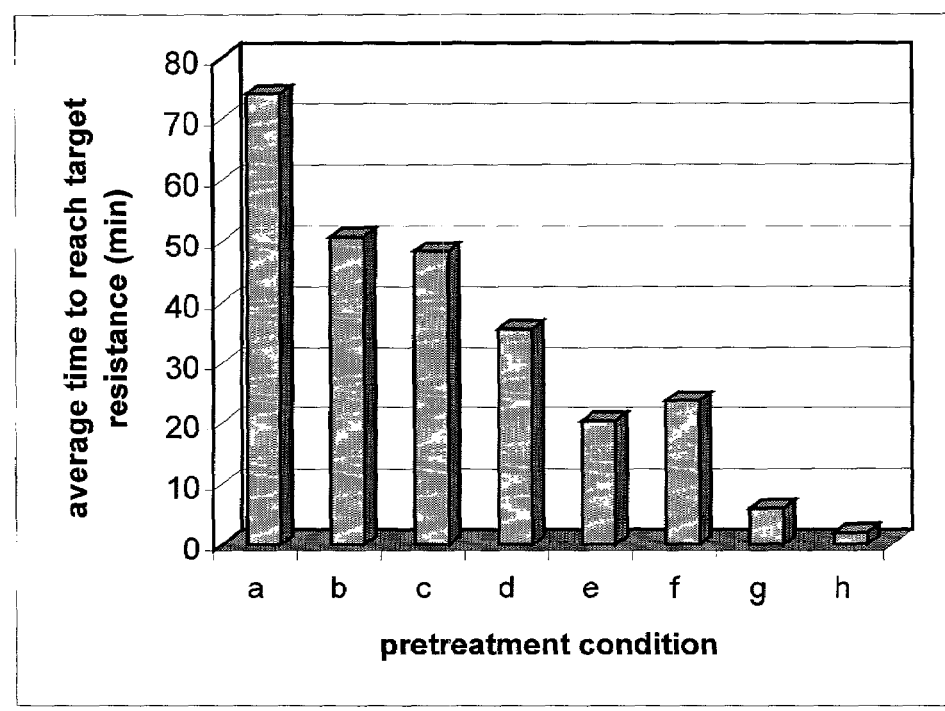
FIG. 11 is a graph indicating the average time to reach target resistance at discomfort threshold voltage. See Table-1 for key to pretreatment conditions.
Figure 12A:
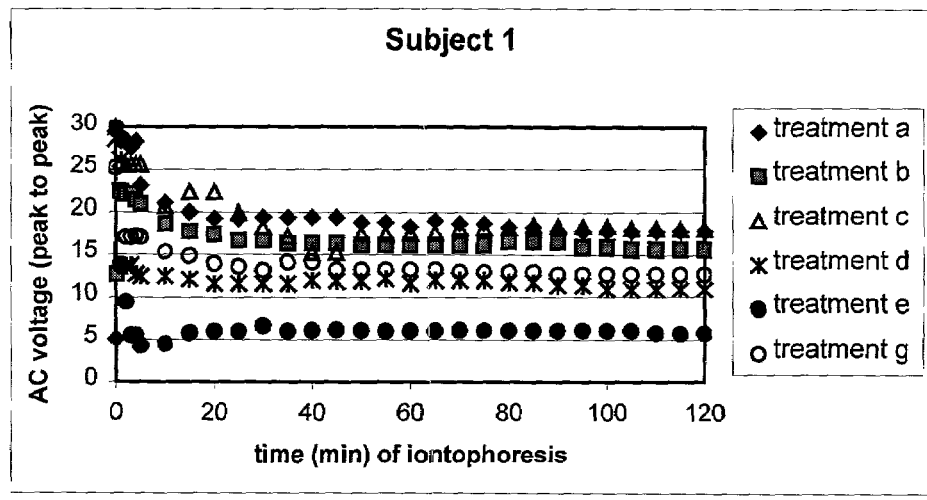
FIGS. 12*a*–12*e* illustrate the AC voltage required to achieve and maintain a target resistance for subjects 1–5, as described in the Examples.
Figure 12B:
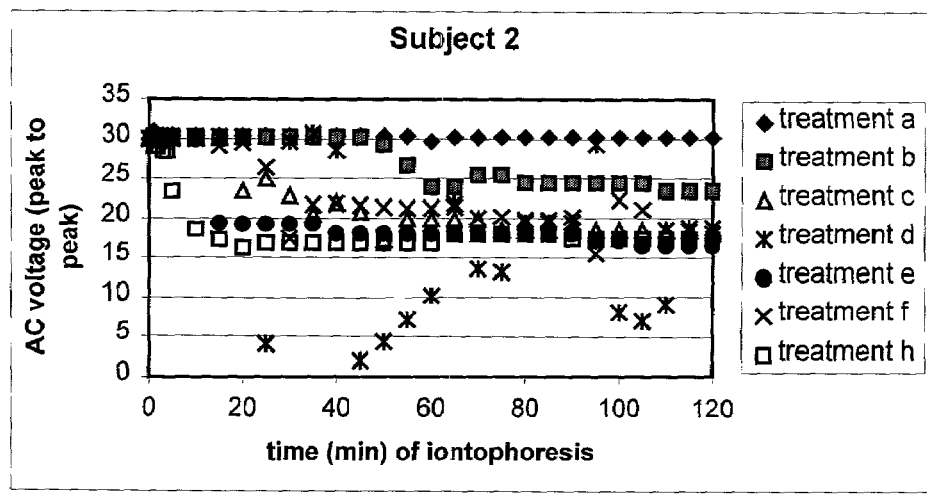
Figure 12C:
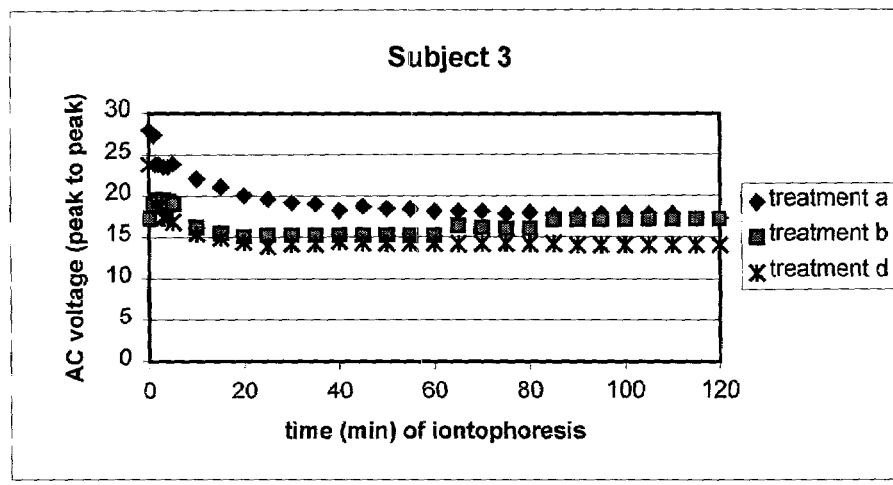
Figure 12D:
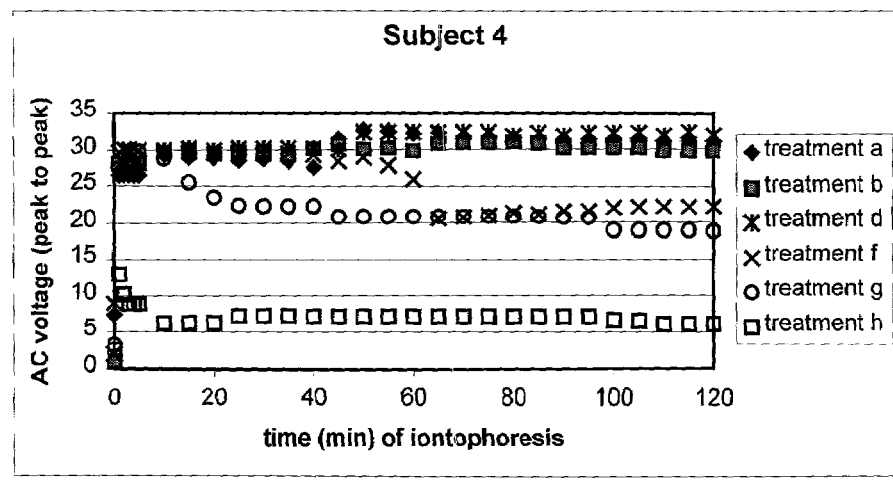
Figure 12E:
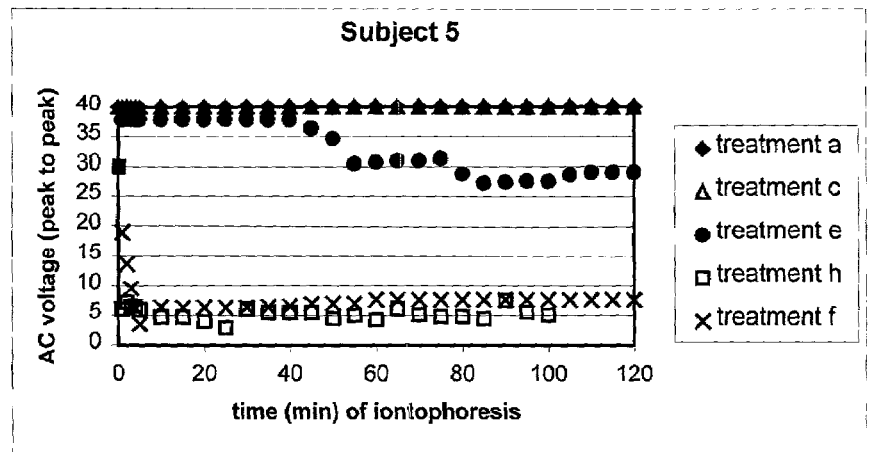

Examination of Table 1 and FIG. 11 reveal that different pretreatment conditions have substantially different effects on the time required to reach target resistance at the AC current discomfort threshold of the test subject. Pretreatment with the positive control 95% ethanol (conditions b and c), yielded no significant difference in time to reach target resistance compared with a no pretreatment control. Of all the groups studied, pretreatment with 1% sodium lauryl sulfate in water for one hour and three hours (group g and h, respectively) produced the greatest reduction in time to target resistance.

Such a reduction in time to target provides for a number of advantages, particularly a reduction in patient discomfort, as well as reduced irritation and/or sensitization.

Decrease in Voltage Required to Maintain Target Resistance

FIGS. 12a–12e illustrate the AC voltage required to achieve and maintain a target resistance of 5 k$\Omega$. All subjects required a relatively high starting AC potential (>20 V) for resistance reduction, although some subjects did not reach the 5 k$\Omega$ target resistance despite application of up to 40 V. Pretreatment with 95% ethanol for one or three hours (treatments b and c respectively) did not substantially lower the required potential to maintain target resistance for times greater than 120 minutes. However, when the essential fatty acid, oleic acid, was added to the formulation, subjects 1 and 2, but not subjects 3 or 4, responded readily with a one-hour pretreatment (treatment d). It was hypothesized that a one-hour pretreatment may not be sufficient for the oleic acid to fully penetrate all layers of the stratum corneum in all subjects. Therefore, a three-hour pretreatment with oleic acid was conducted (treatment e). Subjects 1, 2, and 5 responded readily to the three-hour pretreatment with oleic acid.

It was hypothesized that replacing the ethanol, a relatively hydrophilic carrier, with a more lipophilic carrier might allow the oleic acid to penetrate the stratum corneum more deeply, thereby further increasing its effect. Therefore, a 1:1:1 ratio of oleic acid, propylene glycol, and isopropyl alcohol was formulated. Subjects 4 and 5 responded readily to this combination, although the combination did not prove to be significantly more advantageous for subject 2 than oleic acid in ethanol.

All subjects tested responded readily to the three-hour pretreatment with 1% sodium lauryl sulfate (treatment h), particularly the highly refractive subjects 4 and 5.

Figure 13:
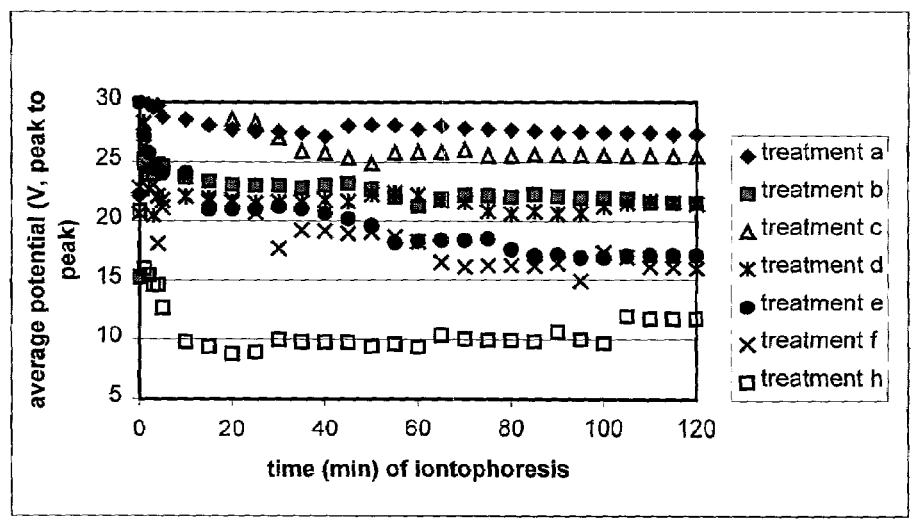
FIG. 13 indicates the average potential for all test subjects for each assistor tested as described in the Examples.

FIG. 13 is a plot of the average potential required for all test subjects for each barrier-modifying agent tested. As may be seen, pretreatment with barrier-modifying agents substantially reduces the voltage needed to achieve and maintain a target resistance of 5 k$\Omega$. The saving in energy required to maintain a target electrical resistance is demonstrated as follows. The average power requirement for achieving the target resistance without a barrier-modifying agent was 155 mW. The average power requirement for a three-hour pretreatment with 1% sodium lauryl sulfate was just 49 mW. The decreased electrical power translates to a net savings of 106 mJ/hour of operation at 5 k$\Omega$ of resistance, a reduction exceeding 2.5 J for a device intended to last 24 hours. It is obvious that such reduction in the electrical requirements of the system will dramatically increase device battery life and thereby decreases battery costs in the device. In addition, the reduced electrical requirements will reduce the sensation experienced by the patient and reduce the incidence of irritation.

We claim:

1. A method of increasing the battery life of an alternating current iontophoretic device used to transport a compound of interest through a localized region of a patient's body tissue, comprising:
    (a) applying an alternating current to a localized region of the body tissue having an inherent barrier limiting the transport of compounds therethrough, the alternating current generated using an alternating current iontophoretic device and applied at a level sufficient both to decrease the electrical resistance of the body tissue to a target resistance level and to maintain the electrical resistance of the body tissue at said target level; and
    (b) either prior to, during, or both prior to and during application of the alternating current, delivering to the localized region of body tissue an amount of at least one barrier-modifying agent effective to alter the penetration barrier so as to reduce the voltage level necessary to achieve and maintain said target resistance level thereby facilitating transport of a compound of interest across the body tissue;
    wherein the barrier-modifying agent is effective to reduce the voltage required to achieve and maintain said target electrical resistance by at least 20% as compared to the voltage required to achieve and maintain said target electrical resistance in the absence of the barrier-modifying agent.

2. The method of claim 1, wherein the barrier-modifying agent is effective to reduce the voltage required to achieve and maintain said target electrical resistance by at least 50% as compared to the voltage required to achieve and maintain said target electrical resistance in the absence of the barrier-modifying agent.

3. The method of claim 2, wherein the barrier-modifying agent is effective to reduce the voltage required to achieve and maintain said target electrical resistance by at least 70% as compared to the voltage required to achieve and maintain said target electrical resistance in the absence of the barrier-modifying agent.

4. The method of claim 1, wherein the body tissue is skin.

5. The method of claim 1, wherein the body tissue is mucosal tissue.

6. The method of increasing the battery life of an alternating current iontophoretic device used to transport a compound of interest through a localized region of a patient's body tissue comprising:
    (a) applying an alternating current to a localized region of the body tissue having an inherent barrier limiting the transport of compounds therethrough, the alternating current generated using an alternating current iontophoretic device and applied at a level sufficient both to decrease the electrical resistance of the body tissue to a target resistance level and to maintain the electrical resistance of the body tissue at said target level; and
    (b) either prior to, during, or both prior to and during application of the alternating current, delivering to the localized region of body tissue an amount of at least one barrier-modifying agent effective to alter the penetration barrier so as to reduce the voltage level necessary to achieve and maintain said target resistance level thereby facilitating transport of a compound of interest across the body tissue;
    wherein the alternating current is applied at a voltage level in the range of about 1 V to about 10 V.

7. The method of claim 6, wherein the alternating current applied is in the range of about 0.1 to 10 V and about 0.01 to 0.5 mA/cm2.

8. A method of increasing the battery life of an alternating current iontophoretic device used to transport a compound of interest through a localized region of a patient's body tissue, comprising:
    (a) applying an alternating current to a localized region of the body tissue having an inherent barrier limiting the transport of compounds therethrough, the alternating current generated using an alternating current iontophoretic device and applied at a level sufficient both to decrease the electrical resistance of the body tissue to a target resistance level and to maintain the electrical resistance of the body tissue at said target level; and
    (b) either prior to, during, or both prior to and during application of the alternating current, delivering to the localized region of body tissue an amount of at least one barrier-modifying agent effective to alter the penetration barrier so as to reduce the voltage level necessary to achieve and maintain said target resistance level thereby facilitating transport of a compound of interest across the body tissue;
    wherein the alternating current is applied to the localized region of the body tissue for a time period in the range of approximately 10 minutes to greater than 24 hours.

9. The method of claim 8, wherein the barrier-modifying agent is delivered to the localized region of body tissue prior to step (a).

10. The method of claim 8, wherein the barrier-modifying agent is delivered to the localized region of body tissue during step (a).

11. The method of claim 8, wherein the barrier-modifying agent is delivered to the localized region of body tissue both prior to and during step (a).

12. The method of claim 8, wherein the barrier-modifying agent is selected from the group consisting of fatty acids, fatty alcohols, bile acids, bile salts, nonionic surfactants, anionic surfactants, cationic surfactants, amphoteric surfactants, hydrocarbon solvents, esters, amides, pyrrolidones, sulfoxides, cyclodextrins, N-alkyl-azacycloalkanones, N-alkyl-azacycloalkenones, urea, alkyl-substituted urea, dialkyl-substituted urea, aryl-substituted urea, diaryl-substituted urea, terpenes, and combinations thereof.

13. The method of claim 12, wherein the barrier-modifying agent is selected from the group consisting of fatty acids, fatty alcohols, bile acids, nonionic surfactants, anionic surfactants, pyrrolidones, and combinations thereof.

14. The method of claim 13, wherein the barrier-modifying agent is a fatty acid.

15. The method of claim 14, wherein the fatty acid is selected from the group consisting of arachidic acid, arachidonic acid, behenic acid, capric acid, caproic acid (n-hexanoic acid), caproleic acid, caprilic acid, docosadienoic acid, docosahexaenoic acid, docosapentaenoic acid, eicosadienoic acid, eicosahexaenoic acid, eicosapentaenoic acid, eicosatrienoic acid, elaidic acid (trans-9-octadecanoic acid), eleosteroic acid, erucic acid, heneicosanoic acid, heptacosanoic acid, heptadecanoic acid, heptanoic acid, hexacosanoic acid, isostearic acid, laurie acid, lignoceric acid, linoleic acid, linoelaidic acid, a-linolenic acid, γ-linolenic acid, myristic acid, myristoleic acid, neodecanoic acid, nervonic acid, nonacosanoic acid, nonadecanoic acid, octacosanoic acid, oleic acid, palmitic acid (n-hexadecanoic acid), palmitoleic acid, pelargonic acid, pentadecanoic acid, pentacosanoic acid, petroselenic acid, phytanic acid, stearic acid, triacontanoic acid, tricosanoic acid, tridecanoic acid, and undecanoic acid, vaccenic acid, and combinations thereof.

16. The method of claim 15, wherein the fatty acid is selected from the group consisting of capric acid, laurie acid, oleic acid, and combinations thereof.

17. The method of claim 13, wherein the barrier-modifying agent is a fatty alcohol.

18. The method of claim 17, wherein the fatty alcohol is selected from the group consisting of behenyl alcohol, cetyl alcohol, elaidyl alcohol, erucyl alcohol, isostearyl alcohol, lauryl alcohol, myristyl alcohol, oleyl alcohol, palmitoleyl alcohol, petroselinyl alcohol, stearyl alcohol, and combinations thereof.

19. The method of claim 13, wherein the barrier-modifying agent is a bile acid or bile salt.

20. The method of 19, wherein the barrier-modifying agent is selected from the group consisting of cholic acid, deoxycholic acid, lithocholic acid, chenodeoxycholic acid, ursodeoxycholic acid, taurocholic acid, taurodeoxycholic acid, taurolithocholic acid, taurochenodeoxycholic acid, tauroursodeoxycholic acid, glycocholic acid, glycodeoxycholic acid, glycolithocholic acid, glycochenodeoxycholic acid, glycoursodeoxycholic acid, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium taurochenodeoxycholate, sodium N-methyl taurocholate, and combinations thereof.

21. The method of claim 13, wherein the barrier-modifying agent is a nonionic surfactant.

22. The method of claim 21, wherein the nonionic surfactant is selected from the group consisting of esters of fatty acids; $C_6$–$C_{22}$ alkyl esters of monohydric alcohols, diols, and polyols; $C_6$–$C_{22}$ alkenyl esters of monohydric alcohols, diols, and polyols; diols esterified with a fatty acid and with a polyoxyalkylene; polyols esterified with a fatty acid and with a polyoxyalkylene; polyoxyalkylene fatty acid esters; polyoxyalkylene fatty ethers; polyglyceryl fatty acid esters; and combinations thereof.

23. The method of claim 22, wherein the nonionic surfactant is selected from the group consisting of cetyl lactate, myristyl lactate, lauryl lactate, isostearyl lactate, stearyl lactate, ethyl lactate, isopropyl myristate, isopropyl palmitate, ethyl linoleate, isopropyl linoleate, methyl laurate, ethyl oleate, isopropyl n-decanoate, isopropyl myristate, isopropyl palmitate, sucrose monooleate, cholesterol stearate, octyldodecyl myristate, propylene glycol dilaurate, propylene glycol monooleate, propylene glycol dioctanoate, propylene glycol dicaprylate, propylene glycol dicaprate, glycerol monolaurate, glycerol monooleate, glycerol monostearate; the sorbitan fatty acid esters sorbitan monopalmitate, sorbitan monooleate, sorbitan dioleate, sorbitan trioleate, sorbitan sesquioleate, sorbitan isostearate, sorbitan diisostearate, sorbitan tristearate, and sorbitan monolaurate; the sucrose fatty acid esters sucrose monooleate, sucrose monostearate, sucrose monolaurate, sucrose distearate, sucrose dipalmitate, sucrose monopalmitate, polyoxyethylene glyceryl fatty acid esters, polyoxypropylene glyceryl fatty acid esters, polyoxyethylene sorbitan fatty acid esters, polyoxypropylene sorbitan fatty acid esters, diethyleneglycol lauryl ether, polyoxyethylene fatty ethers, polyglyceryl fatty acid esters; and combinations thereof.

24. The method of claim 13, wherein the barrier-modifying agent is an anionic surfactant.

25. The method of claim 24, wherein the anionic surfactant is selected from the group consisting of sodium n-dodecyl sulfate, dialkyl sodium sulfosuccinates, sodium lauryl sulfate, sodium 7-ethyl-2-methyl-4-dodecyl sulfate, lithium n-dodecyl sulfate, sodium dodecylbenzene sulfonate, sodium oleate, sodium caprate, sodium laurate, sodium lauryl sarcosinate, sodium dioctyl sulfosuccinate, sodium caproate, sodium caprylate, sodium myristate, sodium myristolate, sodium palmitate, sodium palmitoleate, sodium ricinoleate, sodium linoleate, sodium linolenate, sodium stearate, sodium tetradecyl sulfate, sodium lauryl sarcosinate, sodium docusate, and combinations thereof.

26. The method of claim 13, wherein the barrier-modifying agent is a pyrrolidone.

27. The method of claim 26, wherein the pyrrolidone is selected from the group consisting of 2-pyrrolidone, N-methyl-2-pyrrolidone, 5-methyl-2-pyrrolidone, N-ethyl-2-pyrrolidone, 1,5-dimethyl-2-pyrrolidone, N-hexyl-2-pyrrolidone, N-benzyl-2-pyrrolidone, N-phenyl-2-pyrrolidone, N-lauryl-2-pyrrolidone, 4-carboxy-N-methyl-2-pyrrolidone, 4-carboxy-N-hexyl-2-pyrrolidone, 4-carboxy-N-lauryl-2-pyrrolidone, 4-methoxycarbonyl-N-methyl-2-pyrrolidone, 4-methoxycarbonyl-N-hexyl-2-pyrrolidone, 4-methoxycarbonyl-N-lauryl-2-pyrrolidone, 2-pyrrolidone-5-carboxylic acid and the decyl, oleyl and dodecyl esters thereof, N-famesyl-2-pyrrolidone, 3-hydroxy-N-methyl-2-pyrrolidone, methylthioethyl pyrrolidone, 1-[2-(decylthio)ethyl] azacyclopentan-2-one, 2-mercaptoethylpyrrolidone, 1-dodecyl-2-pyrrolidone, 3-dodecyl-2- pyrrolidone, and combinations thereof.

* * * * *